(12) United States Patent
Hirata et al.

(10) Patent No.: US 9,347,877 B2
(45) Date of Patent: May 24, 2016

(54) LASER GAS ANALYZER

(71) Applicant: Yokogawa Electric Corporation, Musashino-shi, Tokyo (JP)

(72) Inventors: Takaaki Hirata, Musashino (JP); Yasuhiko Mitsumoto, Musashino (JP); Masaya Ooyama, Musashino (JP); Nobuhiko Kanbara, Musashino (JP); Naoyuki Fujimura, Musashino (JP); Minoru Maeda, Musashino (JP); Tadashi Sugiyama, Musashino (JP); Alan Cowie, Friendswood, TX (US); Jie Zhu, Pearland, TX (US)

(73) Assignee: YOKOGAWA ELECTRIC CORPORATION, Tokyo (JP)

( * ) Notice: Subject to any disclaimer, the term of this patent is extended or adjusted under 35 U.S.C. 154(b) by 103 days.

(21) Appl. No.: 13/687,456

(22) Filed: Nov. 28, 2012

(65) Prior Publication Data

US 2013/0135619 A1 May 30, 2013

(30) Foreign Application Priority Data

Nov. 28, 2011 (JP) .................................. 2011-258910

(51) Int. Cl.
*G01N 21/39* (2006.01)
*G01N 21/3504* (2014.01)
*G01N 21/359* (2014.01)

(52) U.S. Cl.
CPC ............ *G01N 21/39* (2013.01); *G01N 21/3504* (2013.01); *G01N 21/359* (2013.01)

(58) Field of Classification Search
CPC .. G01N 21/3504; G01N 21/274; G01N 21/39

USPC .................................. 356/437, 439, 440, 442
See application file for complete search history.

(56) References Cited

U.S. PATENT DOCUMENTS 3,893,771 A * 7/1975 Bell .............................. 356/402
4,061,918 A 12/1977 Preier et al.
(Continued)

FOREIGN PATENT DOCUMENTS

EP 0 401 599 A2 12/1990
JP 51-42588 A 4/1976
(Continued)

OTHER PUBLICATIONS

Extended European Search Report dated Mar. 14, 2013, issued in corresponding European Patent Application No. 12194413.6.
(Continued)

*Primary Examiner* — Roy M Punnoose
(74) *Attorney, Agent, or Firm* — Westerman, Hattori, Daniels & Adrian, LLP

(57) ABSTRACT

A laser gas analyzer includes a wavelength-variable laser having a wide wavelength-variable width, a light-split module configured to split an output light of the wavelength-variable laser into a measurement light and a reference light, a first gas cell into which gases to be measured are introduced, and the measurement light is made to be incident, and a data processor configured to obtain an absorption spectrum of each of the gases to be measured based on a reference signal related to the reference light and an absorption signal related to an output light of the first gas cell, and to obtain concentrations of the respective gases to be measured.

3 Claims, 19 Drawing Sheets

(56) References Cited

U.S. PATENT DOCUMENTS

| | | | |
|---|---|---|---|
| 4,937,448 A * | 6/1990 | Mantz et al. | 250/343 |
| 5,047,639 A * | 9/1991 | Wong | 250/341.1 |
| 5,459,574 A | 10/1995 | Lee et al. | |
| 5,572,031 A * | 11/1996 | Cooper et al. | 250/343 |
| 6,040,915 A * | 3/2000 | Wu et al. | 356/435 |
| 6,107,631 A | 8/2000 | He | |
| 6,800,855 B1 | 10/2004 | Dong et al. | |
| 7,616,316 B1 * | 11/2009 | Silver et al. | 356/437 |
| 7,704,301 B2 * | 4/2010 | Zhou et al. | 95/90 |
| 7,819,946 B2 * | 10/2010 | Zhou et al. | 95/90 |
| 8,013,303 B2 * | 9/2011 | Ershov et al. | 250/339.07 |
| 8,152,900 B2 * | 4/2012 | Zhou et al. | 95/90 |
| 8,500,849 B2 * | 8/2013 | Zhou et al. | 95/90 |
| 2002/0050567 A1 | 5/2002 | Boudet et al. | |
| 2003/0218750 A1 | 11/2003 | Friberg et al. | |
| 2005/0162650 A1 | 7/2005 | Yamamoto | |
| 2007/0081162 A1 * | 4/2007 | Roller et al. | 356/437 |
| 2007/0246653 A1 * | 10/2007 | Zhou | 250/339.1 |
| 2008/0088821 A1 | 4/2008 | Hurvitz et al. | |
| 2008/0259340 A1 * | 10/2008 | Prasad et al. | 356/437 |
| 2008/0304066 A1 | 12/2008 | Kluczynski et al. | |
| 2009/0303487 A1 | 12/2009 | Bond et al. | |
| 2010/0163733 A1 * | 7/2010 | Prasad et al. | 250/345 |
| 2011/0032516 A1 | 2/2011 | Zhou et al. | |
| 2012/0185179 A1 * | 7/2012 | Zhou et al. | 702/24 |

FOREIGN PATENT DOCUMENTS

| | | | | |
|---|---|---|---|---|
| JP | 58-225345 A | | 12/1983 | |
| JP | 60-104238 A | | 6/1985 | |
| JP | 62-280638 A | | 12/1987 | |
| JP | 63-009843 A | | 1/1988 | |
| JP | 01009341 A | * | 1/1989 | G01N 21/39 |
| JP | 01009342 A | * | 1/1989 | G01N 21/39 |
| JP | 01235834 A | * | 9/1989 | G01N 21/39 |
| JP | 2-69639 A | | 3/1990 | |
| JP | 02069639 A | * | 3/1990 | G01N 21/39 |
| JP | 4-364442 A | | 12/1992 | |
| JP | 8-240528 A | | 9/1996 | |
| JP | 9-101259 A | | 4/1997 | |
| JP | 2000-346801 A | | 12/2000 | |
| JP | 2002-107299 A | | 4/2002 | |
| JP | 2005-207982 A | | 8/2005 | |
| JP | 2009-41941 A | | 2/2009 | |
| JP | 2009-216385 A | | 9/2009 | |
| JP | 2010-164480 A | | 7/2010 | |
| WO | 9961895 A1 | | 12/1999 | |

OTHER PUBLICATIONS

Kasyutich, V.L. et al., "Multipass optical cell based upon two cylindrical mirrors for tunable diode laser absorption spectroscopy", Applied Physics B, vol. 88, No. 1, p. 125-130, Apr. 4, 2007; cited in Extended European Search Report dated Mar. 14, 2013.

Kosterev, A.A. et al., "Chemical Sensors Based on Quantum Cascade Lasers", IEEE Journal of Quantum Electronics, vol. 38, No. 6, p. 582-591, Jun. 1, 2002; cited in Extended European Search Report dated Mar. 14, 2013.

Cattaneo, H. et al., "VCSEL based detection of water vapor near 940nm", Molecular and Biomolecular Spectroscopy, vol. 60, No. 14, p. 3269-3275, Dec. 1, 2004; cited in Extended European Search Report dated Mar. 14, 2013.

Japanese Office Action dated Aug. 16, 2013, issued in corresponding Japanese Application No. 2011-258910. (3 pages).

Kazuto Tamura et al., "TDLS200 Tunable Diode Laser Gas Analyzer and its Application to Industrial Process," Yokogawa Technical Report, Yokogawa Electric Corporation, 2010, vol. 53, No. 2(2010), p. 51 to 54 cited in specification w/English Abstract.

Extended European Search Report dated Jul. 20, 2015, issued in counterpart European Patent Application No. 15169921.2 (10 pages).

Extended European Search Report dated Jul. 24, 2015, issued in counterpart European Patent Application No. 15156474.7 (12 pages).

Bond, et al., "Photonic MEMs for NIR in-situ GAS Detection and Identification", IEEE Sensors 2007 Conference, pp. 1368-1371, 2007; cited in Extended European Search Report dated Jul. 20, 2015.

Lytkine et al., "Gas temperature measurements using widely tunable long-wavelength VCSEL", Applied Physics B, vol. 90, pp. 323-327, 2008; cited in Extended European Search Report dated Jul. 20, 2015.

Schilt et al., "Spectral and modulation properties of a largely tunable MEMS-VCSEL in view of gas phase spectroscopy applications", Applied Physics B, vol. 100, pp. 321-329, 2010; cited in Extended European Search Report dated Jul. 20, 2015.

Kögel et al., "Simultaneous Spectroscopy of NH3 and CO Using a > 50 nm Continuously Tunable MEMS-VCSEL", IEEE Sensors Journal, vol. 7, No. 11, pp. 1483-1489, Nov. 2007; cited in Extended European Search Report dated Jul. 20, 2015.

Watanabe T. et al., "A Tunable InP-Based VCSEL with Silicon MEMS Micro Mirror", Optronics, No. 7, pp. 135-140, Jul. 10, (2009), cited in an Office Action issued on Feb. 10, 2016, with a partial English translation. (8 pages).

Notification of Reasons for Refusal dated Feb. 10, 2016, issued in counterpart Japanese Patent Application No. JP2015-049292, with English translation. (9 pages).

* cited by examiner

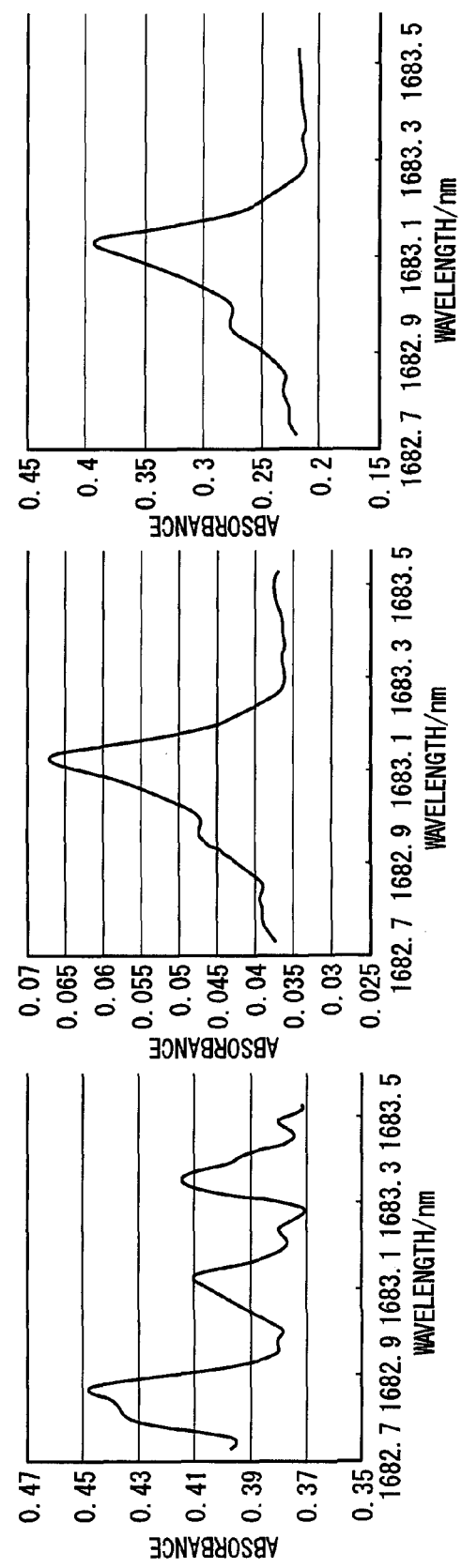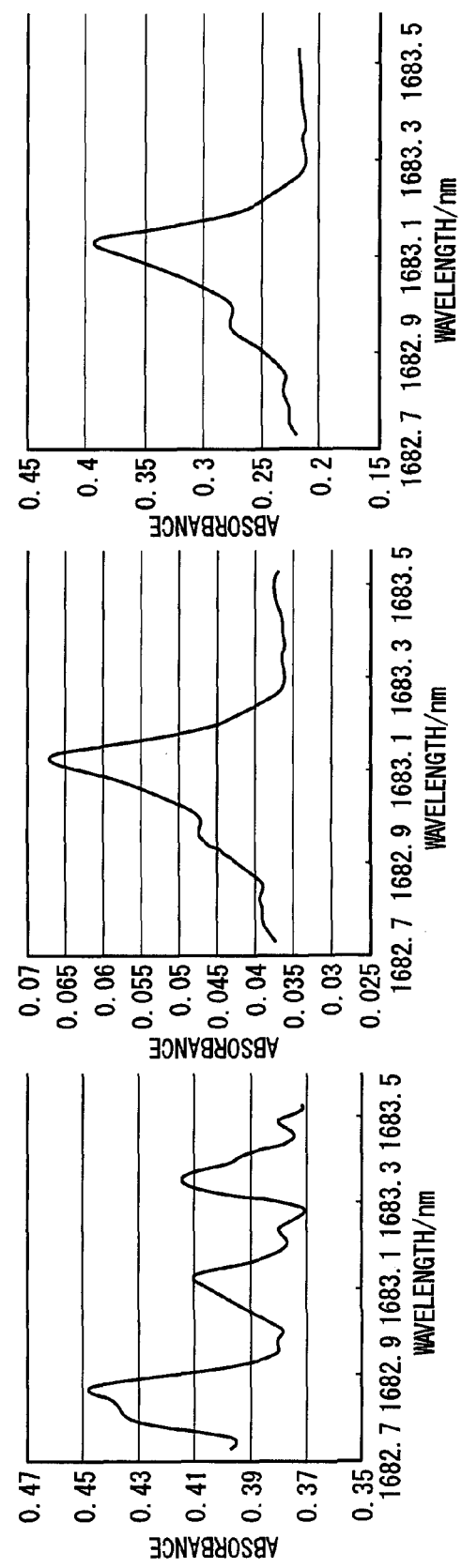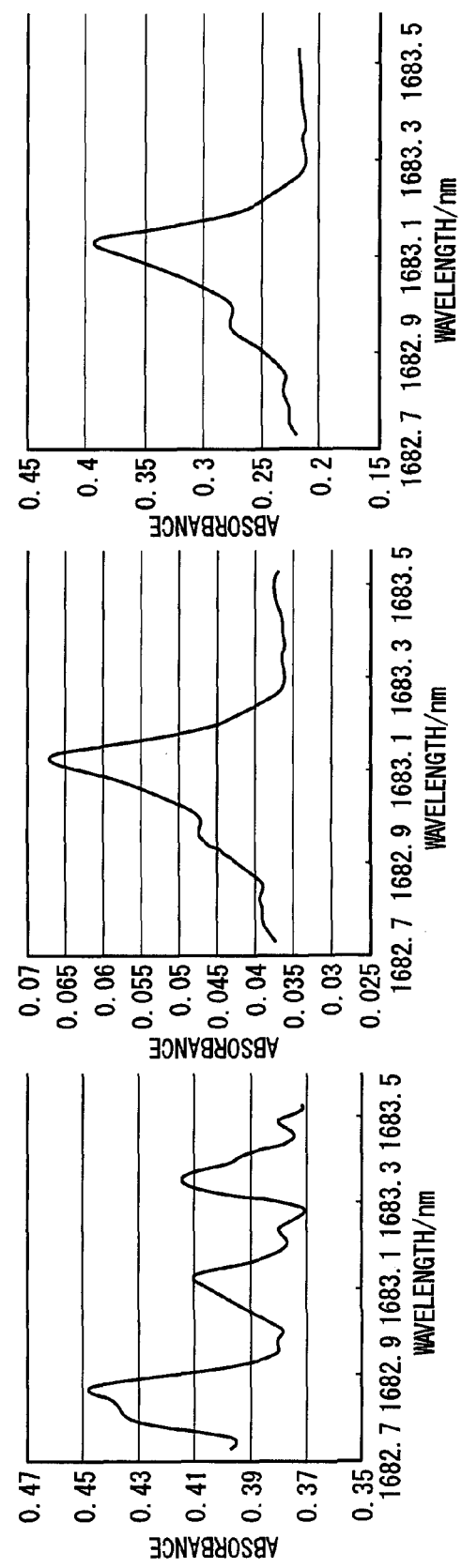

LASER GAS ANALYZER

CROSS-REFERENCE TO RELATED APPLICATION(S)

The present application claims the benefit of priority of Japanese Patent Application No. 2011-258910, filed on Nov. 28, 2011. The disclosures of this application are incorporated herein by reference.

BACKGROUND

1. Technical Field

The present disclosure relates to a laser gas analyzer that can efficiently measure a hydrocarbon multicomponent mixed gas in which multiple hydrocarbon components are mixed.

2. Related Art

A laser gas analyzer using tunable diode laser absorption spectroscopy (TDLAS) method has an advantage of a capability of measuring the concentration of a measurement subject component such as a high-temperature or corrosive gas in a highly component-selective, non-contact, and fast manner on a real time basis without interference by other components simply by irradiating light to a measurement subject from a wavelength-variable semiconductor laser.

FIG. 19 is a block diagram showing an example of a laser gas analyzer of the related art using the TDLAS method, and the laser gas analyzer includes a light source unit including a semiconductor laser that irradiates measurement laser light toward a measurement gas atmosphere, a light-receiving element that detects the measurement laser light which has penetrated through a measurement space of the measurement gas atmosphere, and a detecting unit including a computation processing module that processes output signals of the light-receiving element.

The laser gas analyzer shown in FIG. 19 measures the intrinsic molecular optical absorption spectrums caused by the vibrational and rotational energy transitions of measurement subject component molecules present in an infrared to near infrared range using a semiconductor laser having an extremely narrow oscillation wavelength spectrum line width. The molecular absorption spectrums of most molecules such as $O_2$, $NH_3$, $H_2O$, CO, and $CO_2$ are present in an infrared to near infrared range, and the concentration of a subject component can be computed by measuring the optical absorption amount (absorbance) at a specific wavelength.

In FIG. 19, a semiconductor laser 11 provided in a light source unit 10 irradiates a measurement laser light to the atmosphere of a measurement gas 20. Since the laser light that the semiconductor laser 11 outputs has an extremely narrow oscillation wavelength spectrum line width, and can change the oscillation wavelength by changing the laser temperature or driving current, only one of the respective absorption peaks of the absorption spectrum can be measured.

Therefore, an absorption peak not influenced by an interfering gas can be selected, the wavelength selectivity is high, and there is no influence of other interfering components, and therefore a process gas can be directly measured without removing the interfering gas in a step prior to measurement.

An accurate spectrum that does not overlap with the interfering components can be measured by scanning the oscillation wavelength of the semiconductor laser 11 in the vicinity of one absorption line of the measurement component, but the spectrum shape changes due to a broadening phenomenon of the spectrum which is caused by the measurement gas temperature, the measurement gas pressure, coexisting gas components, and the like. Therefore, in an actual process measurement accompanied by environment changes, correction for the changes is required.

Therefore, the apparatus of FIG. 19 uses a spectrum area method in which the spectrum area is obtained by scanning the oscillation wavelength of the semiconductor laser 11 and measuring the absorption spectrum, and the spectrum area is converted into the component concentration.

Other laser gas analyzers use a peak height method in which a measurement component is obtained from the peak height of an absorption spectrum, or a 2f method in which a wavelength scanning signal is modulated and the concentration of a measurement component is obtained from the peak to peak (P—P) value of the doubled frequency-modulated wave form of the frequency. However, theses methods are liable to be significantly influenced by changes in temperature, pressure, coexisting gas components, and the like.

In contrast, in principle, the spectrum area is not influenced by changes due to the difference of coexisting gas components (the spectrum area is almost constant regardless of the coexisting gas components), and the spectrum area, in principle, also linearly changes with respect to a pressure change.

In the peak height method or the 2f method, the above three factors causing change (temperature, pressure, and coexisting gas components) all have a non-linear influence, and, in a case in which the factors causing change coexist, correction is difficult. However, according to the spectrum area method, linear correction with respect to a gas pressure change and nonlinear correction with respect to a gas temperature change are possible, and accurate correction can be realized.

The measurement laser light that has penetrated through the atmosphere of the measurement gas 20 is received by the light-receiving element 31 provided in a detecting unit 30, and is converted into an electrical signal.

The output signals of the light-receiving element 31 are adjusted to an appropriate amplitude level through a gain-variable amplifier 32, inputted to an A/D convertor 33, and converted into digital signals.

The output data of the A/D convertor 33 are subjected to repetition of a predetermined number (for example, several hundreds to several thousands of times) of integration between an integrator 34 and a memory 35 and storage in the memory 35 in synchronization with scanning of the wavelength of the semiconductor laser 11 so as to remove noise included in measurement signals, and the data are flattened, and then, inputted to a CPU 36.

The CPU 36 performs a computation processing such as the concentration analysis of the measurement gas based on the measurement signals from which noise is removed, and performs the gain adjustment of the amplifier 32 in a case in which the amplitude level of the output signal of the light-receiving element 31 is not appropriate as the input level of the A/D convertor 33.

Non Patent Document 1 describes the measurement principle, features, and specific measurement examples of laser gas analysis to which wavelength-variable semiconductor laser spectroscopy is applied.

RELATED ART DOCUMENT

Non Patent Document

[Non Patent Document 1] Kazuto Tamura, and three other authors, "Laser Gas Analyzer TDLS200 and Its Application to Industrial Processes," Yokogawa Technical Report, Yokogawa Electric Corporation, 2010, Vol. 53, No. 2 (2010), p. 51 to 54

However, in a laser gas analyzer having the configuration shown in FIG. 19, since the wavelength-variable range of the semiconductor laser 11 is narrow, only measurement of a single component is possible.

For example, in a case in which a hydrocarbon multicomponent mixed gas is measured, since the structure is complex, and a number of absorption lines overlap in hydrocarbons other than $CH_4$, broad absorption is present in the base as well as sharp absorption lines, and therefore there is no wavelength having no absorption. Therefore, changes in the base lines due to a change in the transmissivity of gas cells themselves and the like cannot be corrected.

In addition, in a case in which a hydrocarbon multicomponent mixed gas is measured, a method in which the concentrations (gas partial pressures) of the respective hydrocarbons are obtained from an absorption spectrum in which there is broad overlapping absorption of hydrocarbon other than $CH_4$ becomes necessary.

As such a method, a statistical method (chemometrics) was known in the past, but a separate calibration curve needs to be obtained for each application, and therefore excessive engineering man-hours are caused.

On the other hand, for measurement of a single component, an area method which does not rely on the statistical method as described in Non Patent Document 1 is used.

In order to measure the multicomponent mixed gas in which there is broad overlapping absorption using the area method that does not depend on the statistical method, it is necessary to separate the absorption spectrums of the respective components from the overlapped absorption spectrum, and the area method has not yet been put into practical use in analyzers.

SUMMARY

One or more exemplary embodiments of the present invention provide a laser gas analyzer in which a wavelength-variable laser having a wide wavelength-variable width as a laser light source is used, and the concentrations of the respective components included in the multicomponent mixed gas can be measured relatively easily using the area method that does not depend on the statistical method.

A laser gas analyzer according to an exemplary embodiment of the invention comprises:

a wavelength-variable laser having a wide wavelength-variable width;

a light-split module configured to split an output light of the wavelength-variable laser into a measurement light and a reference light;

a first gas cell into which gases to be measured are introduced, and the measurement light is made to be incident; and a data processor configured to obtain an absorption spectrum of each of the gases to be measured based on a reference signal related to the reference light and an absorption signal related to an output light of the first gas cell, and to obtain concentrations of the respective gases to be measured.

The data processor may include;

an absorption line wavelength data storage configured to store absorption line wavelength data of the gases to be measured;

a wavelength calibrator into which the reference signal and the absorption signal are inputted and which is connected to the absorption line wavelength data storage, configured to calibrate wavelength of the absorption spectrum based on the absorption line wavelength data, the reference signal, and the absorption signal, and to obtain an absorption spectrum of an absorbance;

an absorption spectrum data storage configured to stores absorption spectrum data of the gases to be measured;

a spectrum separator into which the absorption spectrum of the absorbance is inputted from the wavelength calibrator and which is connected to the absorption spectrum data storage, and configured to separate the absorption spectrum of the absorbance of each of the gases to be measured from the absorption spectrum of the absorbance;

an area to concentration ratio data storage configure to store wavelength range data used for calculating areas of the absorption lines of the gases to be measured and to store proportional constant data of the area and gas partial pressure; and a concentration detector into which the absorption spectrum of each of the gases to be measured is inputted from the spectrum separator and which is connected to the area to concentration ratio data storage, configured to obtain an area of a designated wavelength range, and to calculate partial pressures of the gases to be measured.

In the laser gas analyzer, the wavelength calibrator may compare an absorption line of a wavelength calibrating gas and known absorption line.

In the laser gas analyzer, the wavelength calibrator may compare the absorption line of the wavelength calibrating gas and known absorption line using polynomial approximation.

In the laser gas analyzer, an absorption rate of a second gas cell in which a wavelength calibrating gas is sealed may be smaller than an absorption rate of the first gas cell.

According to the present invention, it is possible to measure relatively easily the concentrations of the respective components included in the multicomponent mixed gas using the area method that does not depend on the statistical method.

BRIEF DESCRIPTION OF THE DRAWINGS

FIGS. 16A to 16C are spectrum diagrams of ethane which is extracted.

DETAILED DESCRIPTION

Figure 1:
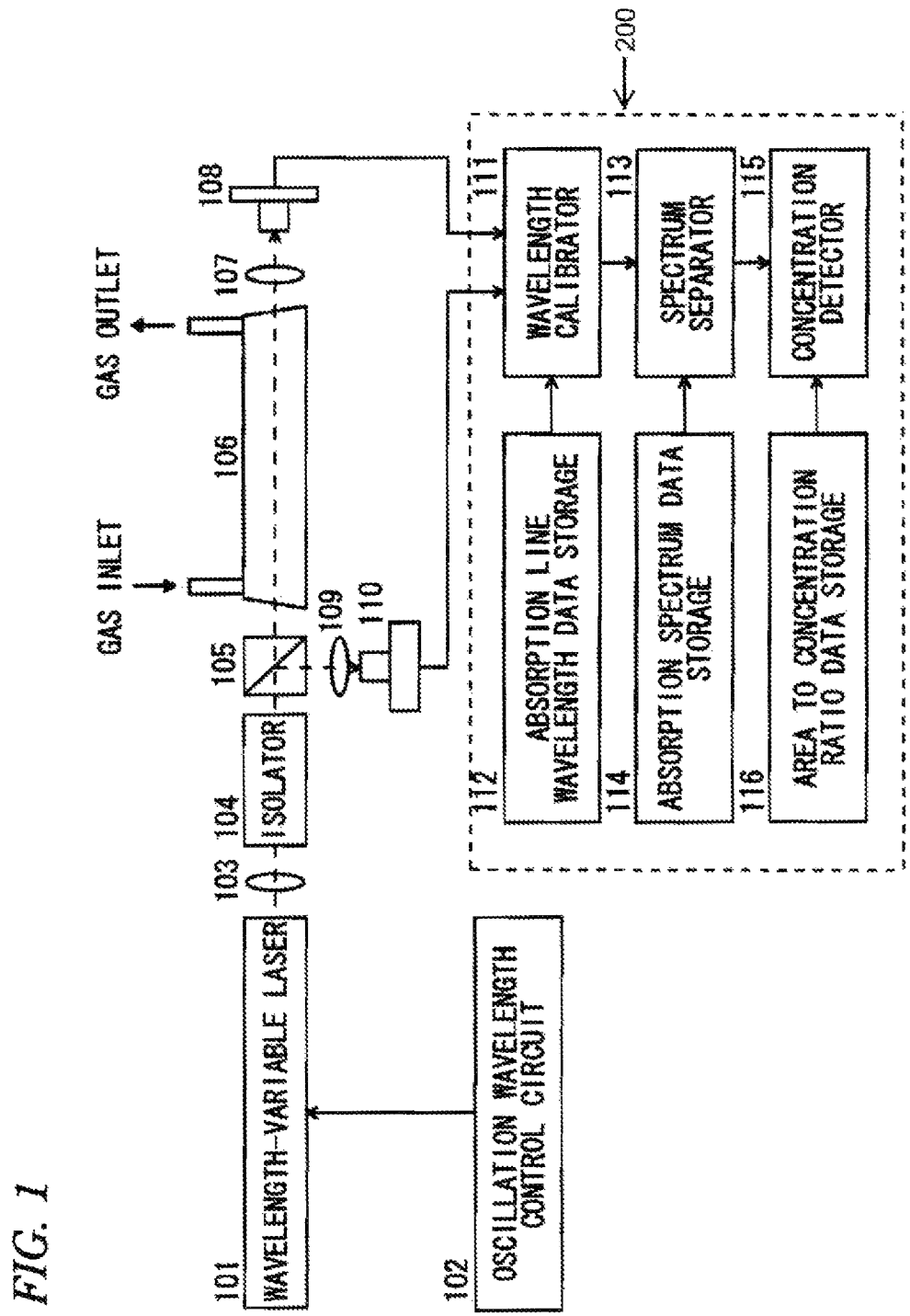
FIG. 1 is a block diagram showing a laser gas analyzer according to an exemplary embodiment of the invention.

Hereinafter, embodiments of the invention will be described in detail using the accompanying drawings. FIG. 1 is a block diagram showing a laser gas analyzer according to an exemplary embodiment of the invention. In FIG. 1, a wavelength-variable laser 101 generates a measurement light of absorption spectrums of gases to be measured, and is connected to an oscillation wavelength control circuit 102 that controls the oscillation wavelength.

The emitted light of the wavelength-variable laser 101 becomes a parallel light at a lens 103, passes through an isolator 104, and is split into two parallel lights of a measurement light and a reference light using a beam splitter 105.

One of the two parallel lights split using the beam splitter 105 is made to be incident to a gas cell 106 into which the gases to be measured are introduced as the measurement light, collected using a lens 107, made to be incident to a photodiode 108 so as to be converted into electrical signals, and inputted into one input terminal of wavelength calibrator 111.

The other parallel light is collected at a lens 109, made to be incident to a photodiode 110 as the reference light, converted into electrical signals, and inputted into the other input terminal of the wavelength calibrator 111.

An absorption line wavelength data storage 112 that stores the absorption line wavelength data of the gases to be measured is connected to the wavelength calibrator 111. The wavelength calibrator 111 calibrates the wavelengths of the spectrum data obtained from the photodiodes 108 and 110 using the absorption line wavelength data stored in the absorption line wavelength data storage 112 and the absorption spectrum obtained from the photodiode 108.

Furthermore, the wavelength calibrator 111 performs division of the wavelength-calibrated spectrum data of the photodiodes 108 and 110 so as to compute the absorbance and obtain the absorption spectrum of the absorbance, and inputs the absorption spectrum of the obtained absorbance into spectrum separator 113.

An absorption spectrum data storage 114 that stores the absorption spectrum data of the gases to be measured is connected to the spectrum separator 113. The spectrum separator 113 separates the absorption spectrums of the absorbance of the gases to be measured from the absorption spectrum of the absorbance inputted from the wavelength calibrator 111 using, for example, least squares fitting in which the absorption spectrums of the gases to be measured are used, and inputs the obtained absorption spectrums of the gases to be measured into concentration detector 115.

An area to concentration ratio data storage 116 is connected to the concentration detector 115. The area to concentration ratio data storage 116 stores wavelength range data that calculate the areas of the absorption lines of the respective gases to be measured, and stores the proportional constant data of the area and the gas partial pressure. The concentration detector 115 obtains the area of a designated wavelength range from the absorption spectrums of the absorbance of the respective gases to be measured inputted from the spectrum separator 113, and, then, computes the partial pressures of the gases to be measured by multiplying the obtained area by a designated proportional constant. A data processor 200 of the laser gas analyzer shown in FIG. 1 includes the wavelength calibrator 111, the absorption line wavelength data storage 112, the spectrum separator 113, the absorption spectrum data storage 114, the concentration detector 115 and the area-to-concentration ratio data storage 116.

Figure 2:
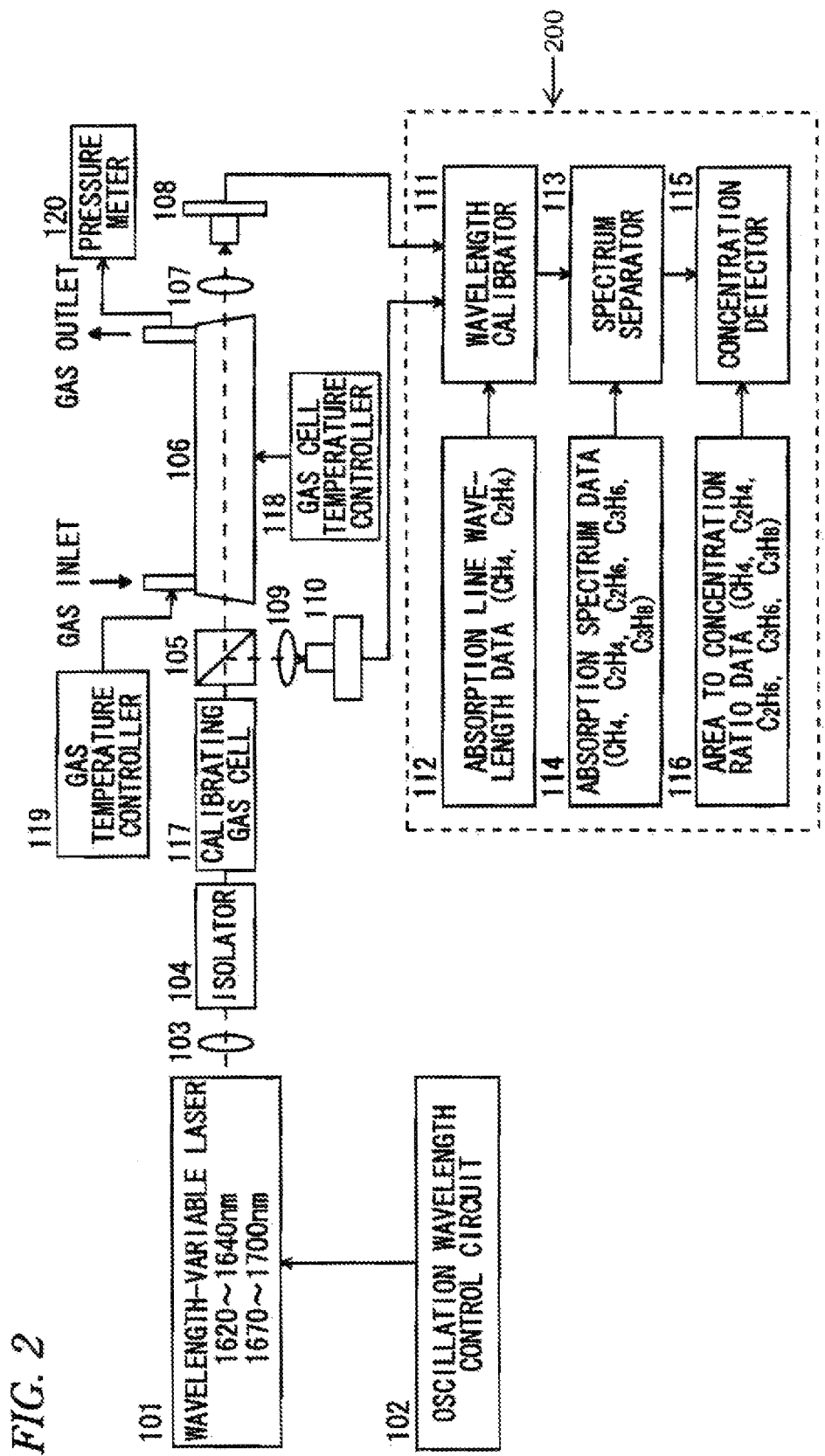
FIG. 2 is a block diagram showing a specific example of the laser gas analyzer according to the exemplary embodiment of the invention.

FIG. 2 is a block diagram showing a specific example of the laser gas analyzer according to the embodiment of the invention which measures multiple hydrocarbon component, and the same signs are given to portions that are common in FIG. 1. The wavelength-variable laser 101 includes a first MEMS-vertical cavity surface emitting laser (MEMS-VCSEL) that emits a wavelength of 1620 nm to 1640 nm at which the measurement light of the absorption spectrum of hydrocarbon is generated and a second MEMS-VCSEL that emits a wavelength of 1670 nm to 1700 nm. The respective MEMS-VCSELs are connected to the oscillation wavelength control circuit 102, the oscillation wavelength control circuit 102 alternately applies a current to the respective MEMS-VCSELs so as to alternately oscillate the respective MEMS-VCSELs, and controls a voltage applied to the oscillating MEMS-VCSELs so as to control the respective oscillating wavelengths.

The emitted light of the respective MEMS-VCSEL becomes a parallel light at the lens 103, passes through the isolator 104, furthermore, passes through a wavelength calibrating gas cell 117 having $CH_4$ and $C_2H_4$ sealed therein, and is split into two parallel lights of a measurement light and a reference light using the beam splitter 105.

One of the two parallel lights split using the beam splitter 105 is made to be incident to the gas cell 106 into which the gases to be measured are introduced as the measurement light, and becomes the absorption signals of the gases to be measured. The output light of the gas cell 106 is collected using the lens 107, made to be incident to the photodiode 108 so as to be converted into electrical signals, and inputted into one input terminal of the wavelength calibrator 111.

The other parallel light is collected at the lens 109, made to be directly incident to the photodiode 110 as the reference light, converted into electrical signals, and inputted into the other input terminal of the wavelength calibrator 111. Thereby, the reference signals of the output light intensity of the respective MEMS-VCSELs are formed.

The gas cell 106 is controlled to a predetermined temperature through a gas cell temperature controller 118, and the gases to be measured are controlled to the same temperature as the gas cell 106 through a gas temperature controller 119.

Among the gases to be measured, the absorption line wavelength data of $CH_4$ and $C_2H_4$ that is sealed as wavelength calibrating gas in the wavelength calibrating gas cell 117 are stored in the absorption line wavelength data storage 112 connected to the wavelength calibrator 111. The wavelength calibrator 111 calibrate the wavelengths of the spectrum data obtained from the photodiodes 108 and 110 using the absorption line wavelength data of $CH_4$ and $C_2H_4$ stored in the absorption line wavelength data storage 112 and the absorption spectrums of $CH_4$ and $C_2H_4$ obtained from the photodiode 110.

Furthermore, the wavelength calibrator 111 performs division of the wavelength-calibrated spectrum data of the photodiodes 108 and 110 so as to compute the absorbance and obtain the absorption spectrum of the absorbance of the gases to be measured, and inputs the obtained absorption spectrums of the absorbance of the gases to be measured into the spectrum separator 113.

The absorption spectrum data storage 114 connected to the spectrum separator 113 stores the absorption spectrum data of hydrocarbon components ($CH_4$, $C_2H_4$, $C_2H_6$, $C_3H_6$, and $C_3H_8$) which are the gases to be measured. The spectrum separator 113 separates the absorption spectrums of the absorbance of the respective hydrocarbon components ($CH_4$, $C_2H_4$, $C_2H_6$, $C_3H_6$, and $C_3H_8$) from the absorption spectrum of the absorbance inputted from the wavelength calibrator 111 using least squares fitting in which the absorption spectrums of the gases to be measured are used, and inputs the obtained absorption spectrums of the respective gases to be measured into the concentration detector 115.

The area to concentration ratio data storage 116 connected to the concentration detector 115 stores wavelength range data that calculate the areas of the absorption lines of the hydrocarbon components ($CH_4$, $C_2H_4$, $C_2H_6$, $C_3H_6$, and $C_3H_8$) which are the respective gases to be measured and stores the proportional constant data of the area and the gas partial pressure which has been actually measured in advance.

The concentration detector 115 obtains the area of a designated wavelength range from the absorption spectrums of the absorbance of the respective gases to be measured inputted from the spectrum separator 113, and obtains the partial pressures of the respective gases to be measured by multiplying the obtained area by a designated proportional constant. Furthermore, the concentrations of the respective gases to be measured can be obtained by dividing the obtained partial pressures of the respective gases to be measured by the total pressure measured using a pressure meter 120 provided in the outlet path of the gas cell 106.

Figure 3:
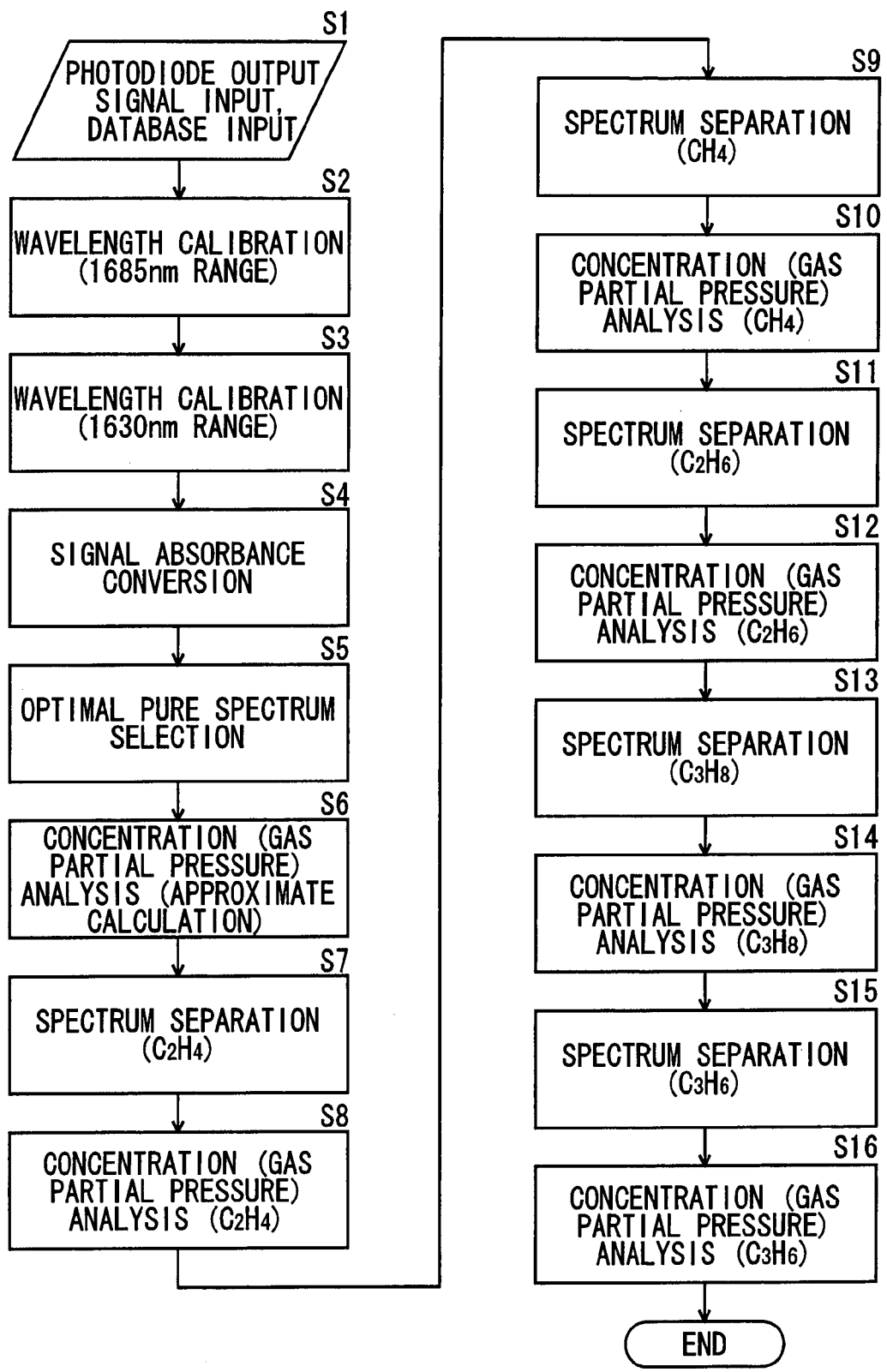
FIG. 3 is a flowchart explaining the entire flow of a measurement operation of the analyzer as shown in FIG. 2.

FIG. 3 is a flowchart explaining the entire flow of a measurement operation of the analyzer as shown in FIG. 2. The processing of signals starts wavelength calibration using the reference signals that are not influenced by the gases to be measured.

The wavelength calibrator 111 detects the data numbers of the peaks of the sharp absorption spectrums of $CH_4$ and $C_2H_4$ based on the reference signals outputted from the photodiode 110, and determines the accurate wavelengths of the data numbers from the table of absorption lines and wavelengths. From the relationship between the obtained plural data numbers and the wavelengths, the respective data numbers, for example, a wavelength 1685 nm range, and a 1630 nm range are matched using polynomial approximation (Steps S1 to S3).

After wavelength calibration, absorbance is calculated from the reference signals and the absorption signals in the respective wavelength bands (Step S4), an optimal pure spectrum is selected (Step S5), a rough gas concentration analysis is performed (Step S6), and then spectrum separation and concentration analyses are repeated sequentially ($C_2H_4 \to CH_4 \to C_2H_6 \to C_3H_8 \to C_3H_6$) from components having a larger influence (Steps S7 to S16).

When the incident intensity to the gas to be measured is represented by $I_1$, the light intensity transmitted through the gas to be measured is represented by $I_2$, and the transmissivity of the gas to be measured is represented by A, the absorbance of the gas at a wavelength λ, becomes $$\text{Absorbance} = \log_{10}[I_1(\lambda)/I_2(\lambda)] \quad (1)$$
$$= \log_{10}[I_1(\lambda)/I_1(\lambda) \times A(\lambda)]$$
$$= \log_{10}[1/A(\lambda)]$$

Furthermore, when the light intensity of the reference light is represented by $I_r$, the light intensity immediately before the wavelength calibrating gas cell 117 is represented by $I_0$, the transmissivity of the wavelength calibrating gas is represented by $A_1$, the transmissivity of the wavelength calibrating gas cell 117 is represented by $T_{r1}$, the split ratio by the beam splitter 105 is represented by $R_1:R_2$ ($R_1+R_2=1$), and the transmissivity of the gas cell 106 is represented by $T_r$, it is possible to express $$I_r(\lambda) = I_0(\lambda) \times A_1(\lambda) \times T_{r1} \times R_1(\lambda) \quad (2)$$

$$I_2(\lambda) = I_0(\lambda) \times A_1(\lambda) \times T_{r1} \times R_2(\lambda) \times A(\lambda) \times T_r(\lambda) \quad (3)$$

Therefore, $$\log_{10}[I_r(\lambda)/I_2(\lambda)] = \log_{10}[R_1(\lambda)/R_2(\lambda) \times A(\lambda) \times T_r(\lambda)] \quad (4)$$
$$= \log_{10}[1/A(\lambda)] + \log_{10}[R_1(\lambda)/R_2(\lambda) \times T_r(\lambda)]$$
$$= \text{absorbance} + \text{analyzer function}$$

Herein, since the second element does not depend on the gas to be measured, when a spectrum is obtained in advance by sealing a gas for which absorption can be ignored in the gas cell, the second element can be removed. That is, when the common logarithm is calculated by obtaining the ratio of the output signals of the photodiodes 108 and 110 like the first element in the formula (4), the absorbance is obtained.

Meanwhile, attention should be paid to that there are cases in which both of $I_r$ and $I_2$ include the influence of the wavelength calibrating gas cell 117. Due to the above fact, like the first element in the formula (4), when the ratio of both signals is obtained, the signals of the wavelength calibrating gas cell 117 disappear, and therefore calculation can be performed easily.

Next, the wavelength bands used when the concentrations (gas partial pressures) of the respective hydrocarbons are detected will be described. The point of the invention is that it is possible to separate the spectrum of each of the respective gases to be measured (hydrocarbons) from the measured absorption spectrum of the mixed gas, and obtain the concentrations (gas partial pressures) from the area of each of the obtained absorption lines.

In order to precisely separate spectrums, wavelength bands in which the characteristic absorption lines of the gases to be measured are present, but the characteristic absorption lines of other mixed gas are not present are preferably selected. When such wavelength bands are selected, since the major influence of the other gases becomes the same as that of a change in the base line, the influence of the other gases can be minimized by employing a concentration (gas partial pressure) detecting method which is not influenced by a change in the base line. Therefore, in the invention, the concentrations (gas partial pressures) are detected using different wavelength bands satisfying the above conditions for each of the gases to be measured (hydrocarbons) and a method which is not influenced by a change in the base line. Hereinafter, the above will be described respectively.

Figure 4A:
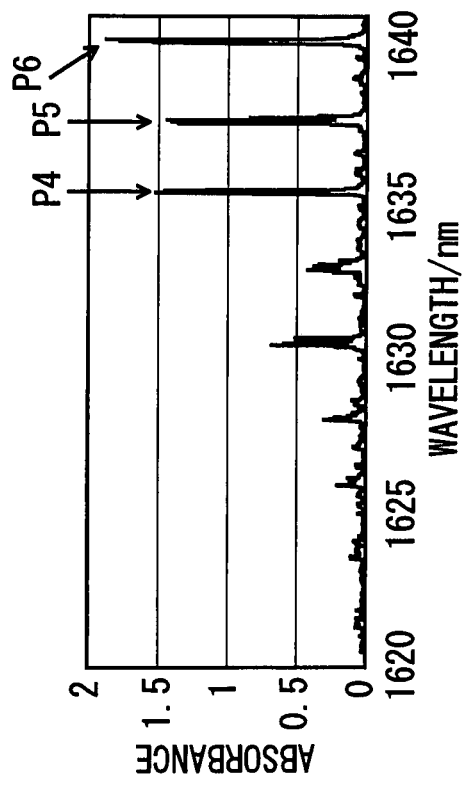
FIGS. 4A and 4B are spectrum diagrams of methane.
Figure 4B:
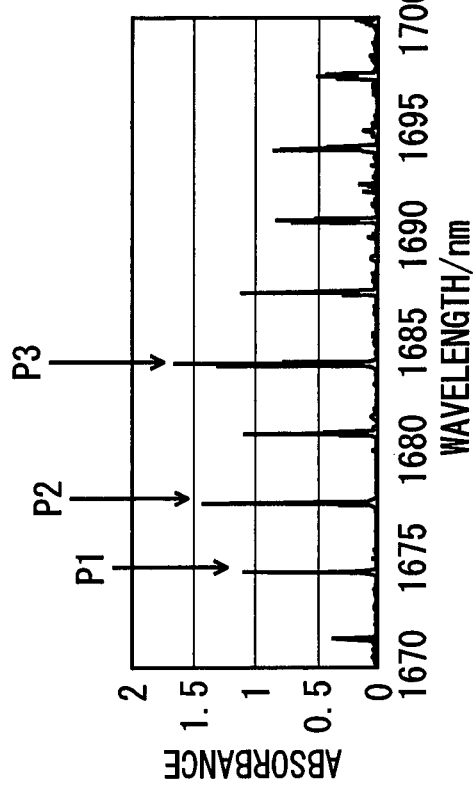

FIGS. 4A and 4B show the spectrum diagrams of methane, in which FIG. 4A indicates the 1685 nm band, and FIG. 4B indicates the 1630 nm band. As is evident from FIG. 4, methane has plural sharp peaks in each of the wavelength bands. Among the sharp peaks, sharp peaks having a small amount of the absorption components of the other gases and that are appropriate for the concentrations (gas partial pressures) detection are Peaks P1 to P6 which are indicated using arrows.

Figure 5:
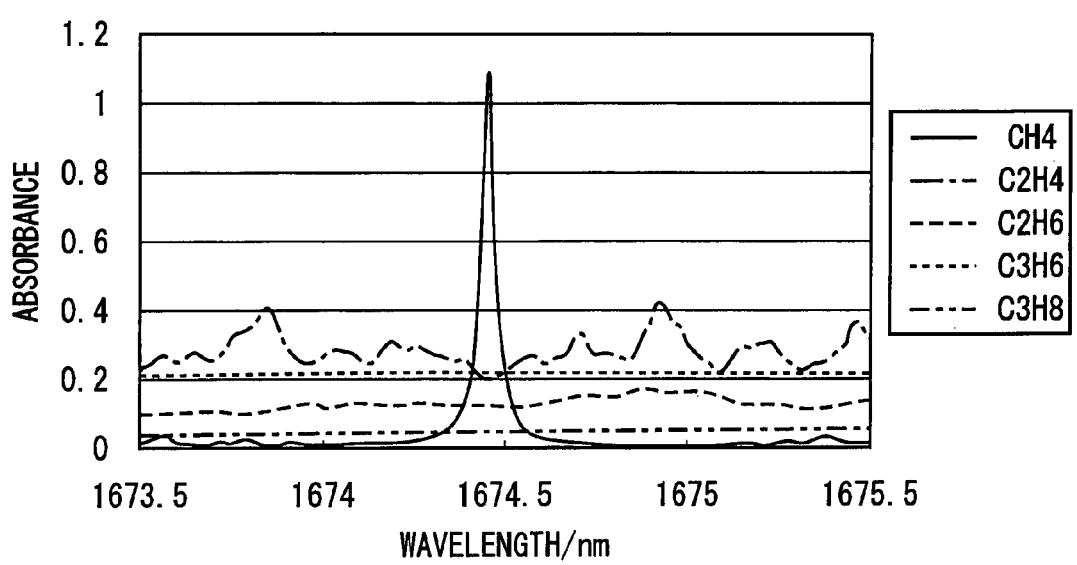
FIG. 5 is a spectrum diagram of methane, ethylene, ethane, propylene, and propane in the vicinity of 1674.5 nm of Peak P1 in FIG. 4A.

FIG. 5 is a spectrum diagram of methane, ethylene, ethane, propylene, and propane in the vicinity of 1674.5 nm of Peak P1 in FIG. 4. According to FIG. 5, it is found that the peak of methane is evidently sharp and large compared to those of other gas spectrums. Thereby, the influence of other gases can be considered to be a change in the base line.

Figure 6B:
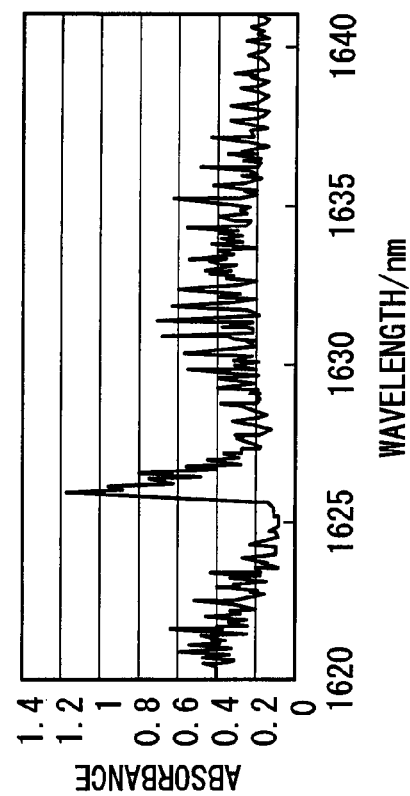
FIGS. 6A and 6B are spectrum diagrams of ethylene.
Figure 6A:
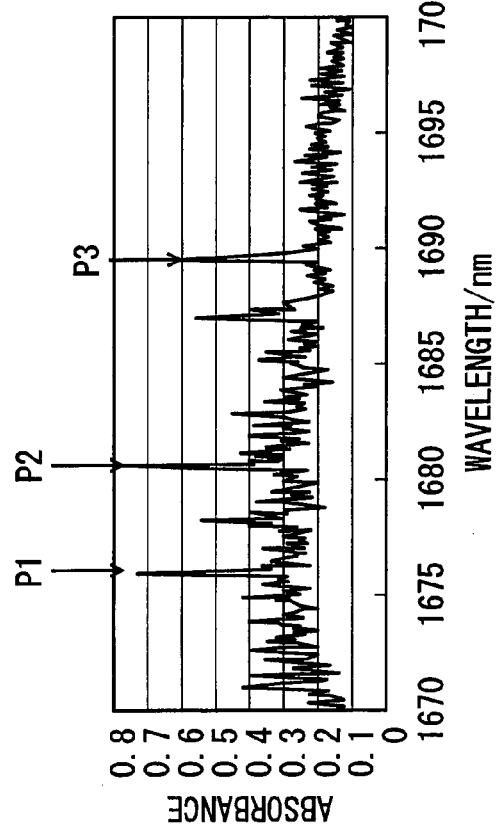

FIGS. 6A and 6B show the spectrum diagrams of ethylene, in which FIG. 6A indicates the 1685 nm band, and FIG. 6B indicates the 1630 nm band. As is evident from FIG. 6, ethylene also has plural sharp peaks in each of the wavelength bands; however, in the 1630 nm band, since the peak intervals are narrow, it is difficult to extract specific peaks. In contrast to the above, Peaks P1 to P3 indicated using arrows in the 1685 nm band are appropriate for concentration (gas partial pressure) detection.

Figure 7:
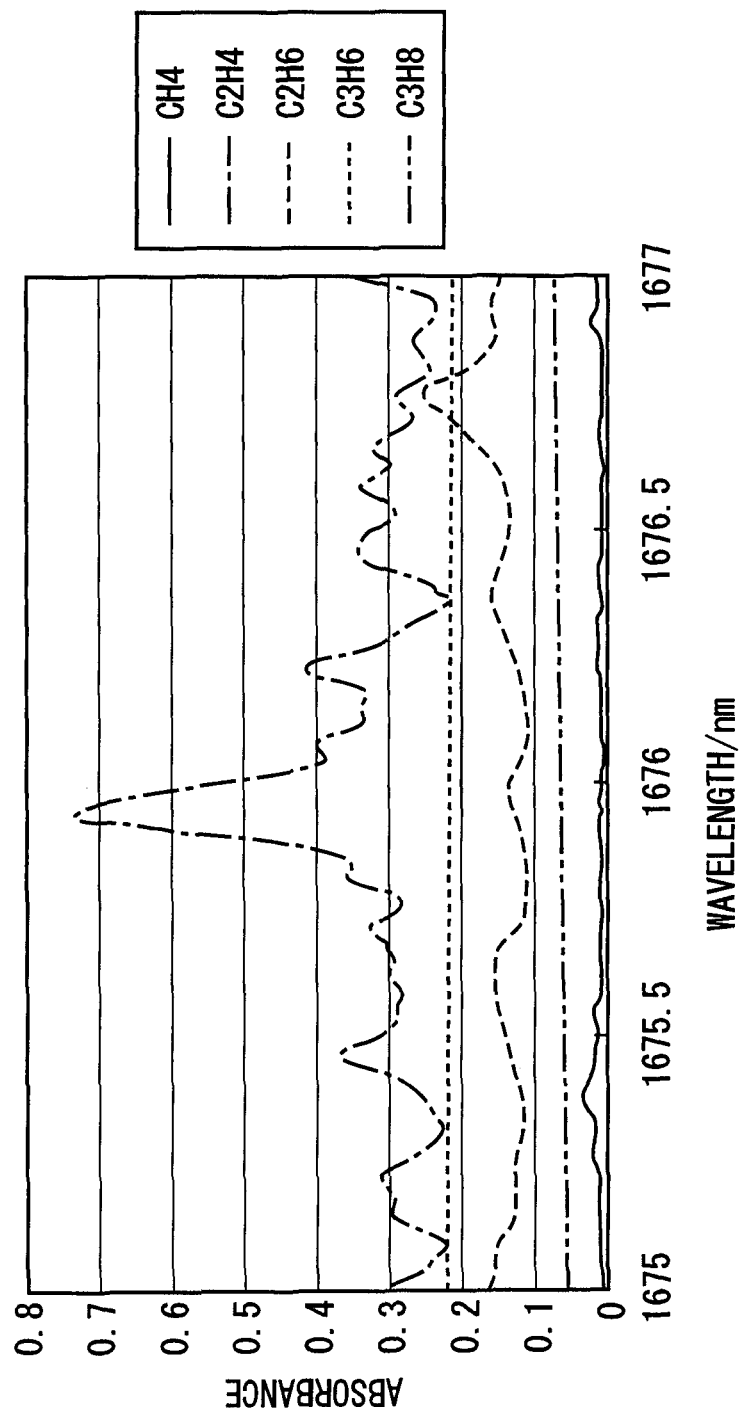
FIG. 7 is a spectrum diagram of methane, ethylene, ethane, propylene, and propane in the vicinity of 1675.9 nm of Peak P1 in FIG. 6A.

FIG. 7 is a spectrum diagram of methane, ethylene, ethane, propylene, and propane in the vicinity of 1675.9 nm of Peak P1 in FIG. 6. According to FIG. 7, it is found that the peak of ethylene is evidently sharp and large compared to those of other gas spectrums. Thereby, among the sharp peaks, Peak P1 can be said to have a small amount of the absorption components of other gases and be appropriate for concentration (gas partial pressure) detection.

Figure 8A:
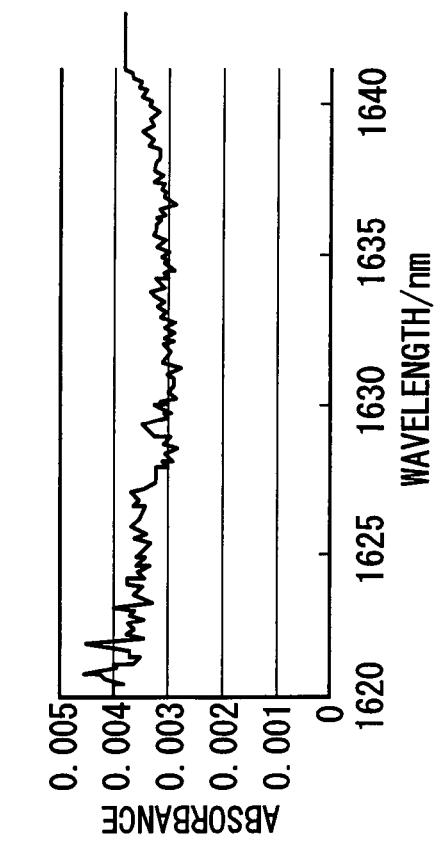
FIGS. 8A and 8B are spectrum diagrams of ethane.
Figure 8B:
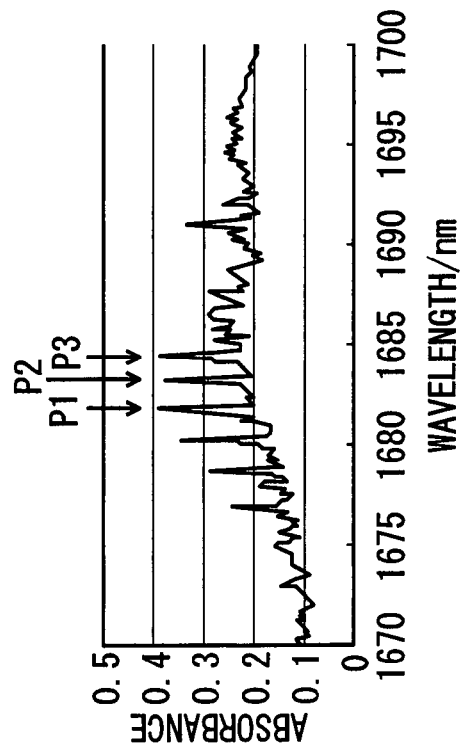

FIGS. 8A and 8B show the spectrum diagrams of ethane, in which FIG. 8A indicates the 1685 nm band, and FIG. 8B indicates the 1630 nm band. As is evident from FIG. 8, ethane has no peak in the 1630 nm band, and has several peaks in the 1685 nm band. Among the peaks, Peaks P1 to P3 indicated using arrows are appropriate for concentration (gas partial pressure) detection.

Figure 9:
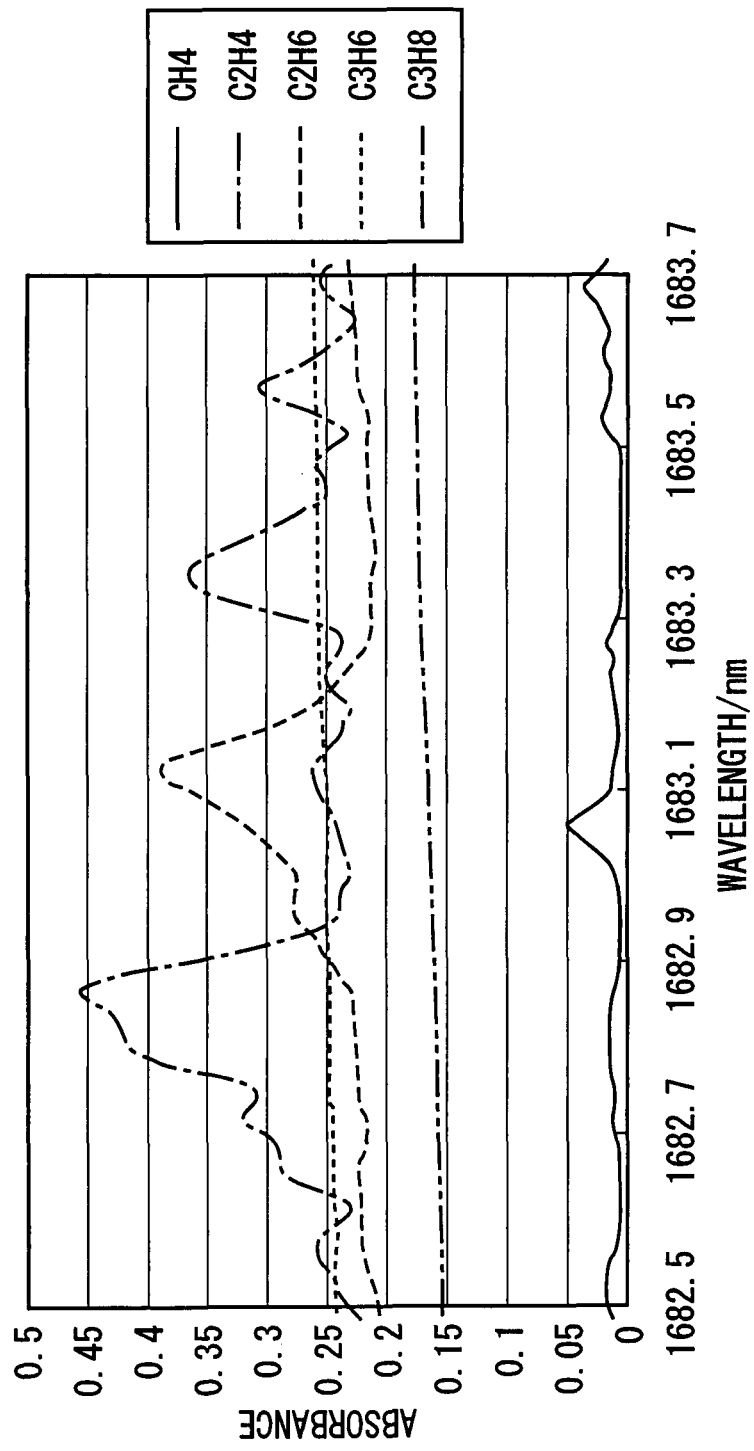
FIG. 9 is a spectrum diagram of methane, ethylene, ethane, propylene, and propane in the vicinity of 1683.1 nm of Peak P2 in FIG. 8A.

FIG. 9 is a spectrum diagram of methane, ethylene, ethane, propylene, and propane in the vicinity of 1683.1 nm of Peak P2 in FIG. 8. According to FIG. 9, ethylene and methane have absorption in the vicinity of 1683.1 nm, and the absorption of ethane is highest.

Figure 10B:
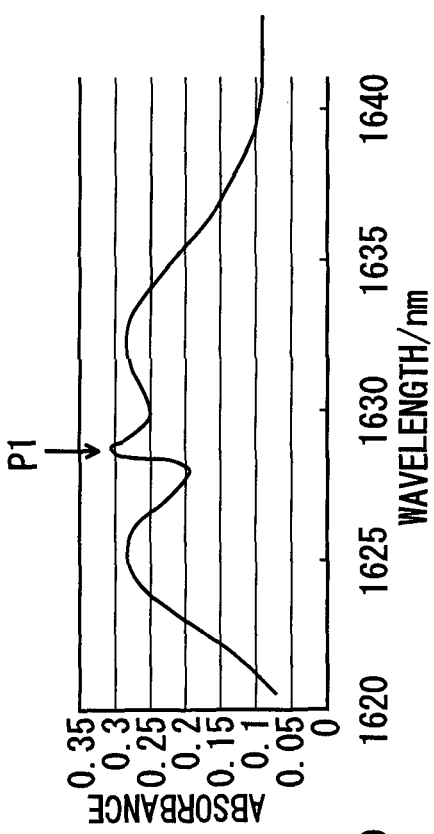
FIGS. 10A and 10B are spectrum diagrams of propylene.
Figure 10A:
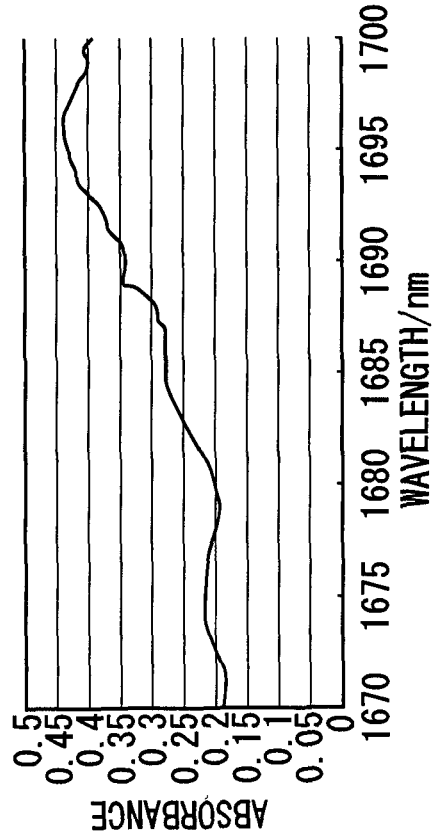

FIGS. 10A and 10B show the spectrum diagrams of propylene, in which FIG. 10A indicates the 1685 nm band, and FIG. 10B indicates the 1630 nm band. As is evident from FIG. 10, propylene has only one peak at 1628.7 nm, and this peak is used for concentration (gas partial pressure) detection.

Figure 11:
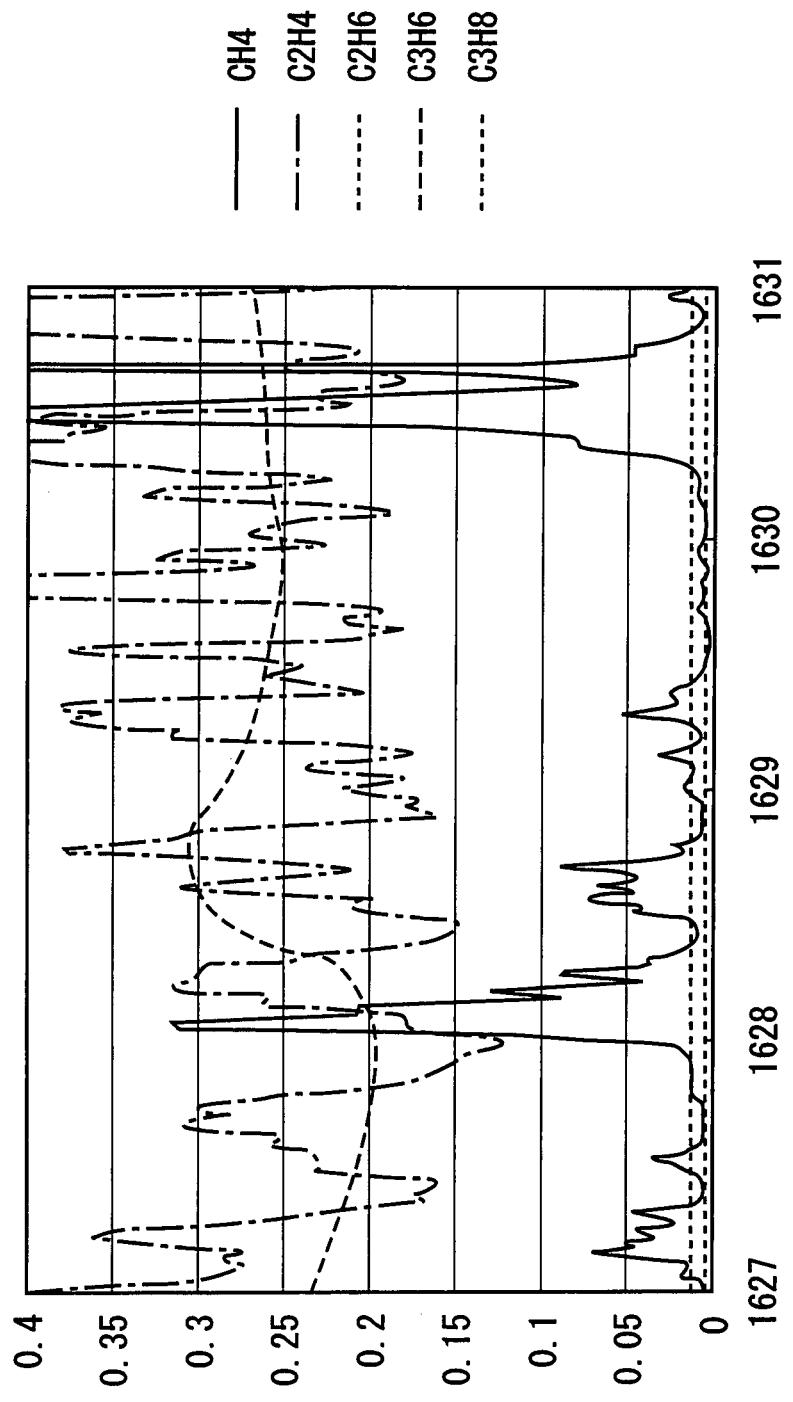
FIG. 11 is a spectrum diagram of methane, ethylene, ethane, propylene, and propane in the vicinity of the peak of propylene in FIG. 10B.

FIG. 11 is a spectrum diagram of methane, ethylene, ethane, propylene, and propane in the vicinity of the peak of propylene in FIG. 10. According to FIG. 11, since absorptions of ethylene and methane are large, a method in which propylene is extracted by removing the influence of these gases becomes important.

Figure 12B:
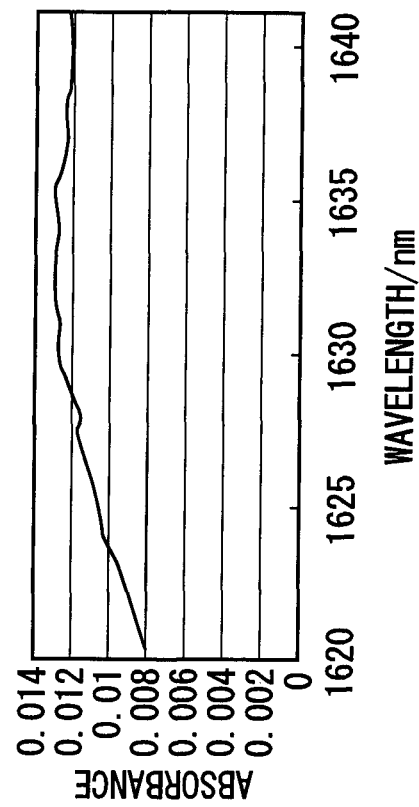
FIGS. 12A and 12B are spectrum diagrams of propane.
Figure 12A:
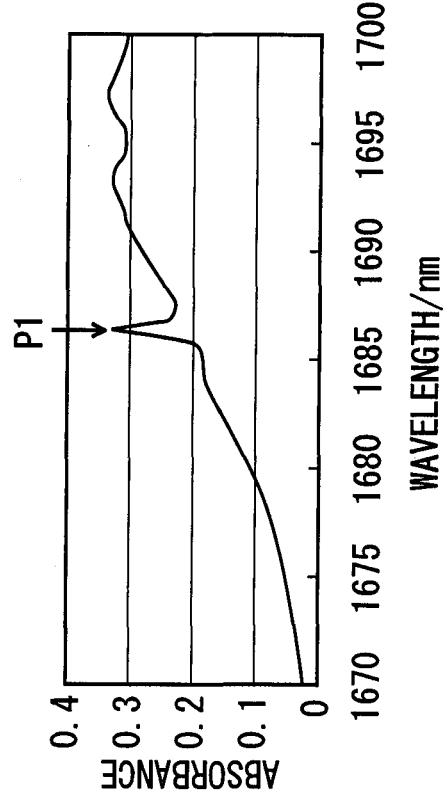

FIGS. 12A and 12B show the spectrum diagrams of propane, in which FIG. 12A indicates the 1685 nm band, and FIG. 12B indicates the 1630 nm band. As is evident from FIG. 12, propane has only one peak at 1686.4 nm, and this peak is used for concentration (gas partial pressure) detection.

Figure 13:
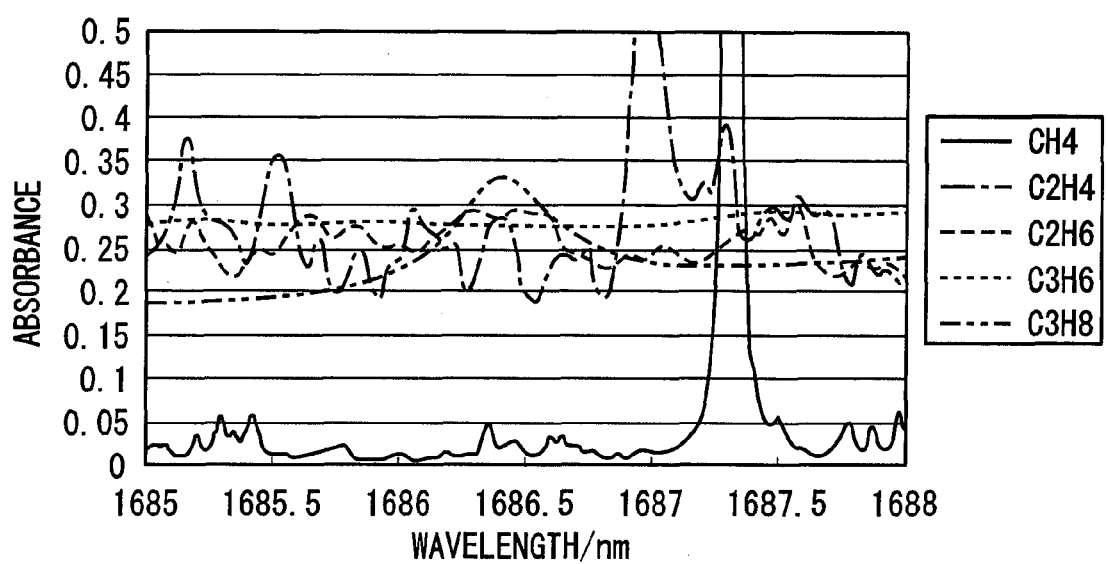
FIG. 13 is a spectrum diagram of methane, ethylene, ethane, propylene, and propane in the vicinity of the peak of propane in FIG. 12A.

FIG. 13 is a spectrum diagram of methane, ethylene, ethane, propylene, and propane in the vicinity of the peak of propane in FIG. 12. According to FIG. 13, since absorptions of ethylene and methane are large, a method in which propane is extracted by removing the influence of these gases becomes important.

Next, a spectrum separation method will be described. Here, attention should be paid to that the shape of the absorption spectrum changes due to total pressure, gas concentrations (gas partial pressures), and the kinds of the mixed gas. When the changes are not dealt with, precise spectrum separation is not possible.

Therefore, in the invention, the absorption spectrums of the respective gases to be measured in consideration of a change in the spectrum shape are used for spectrum separation.

Figure 14:
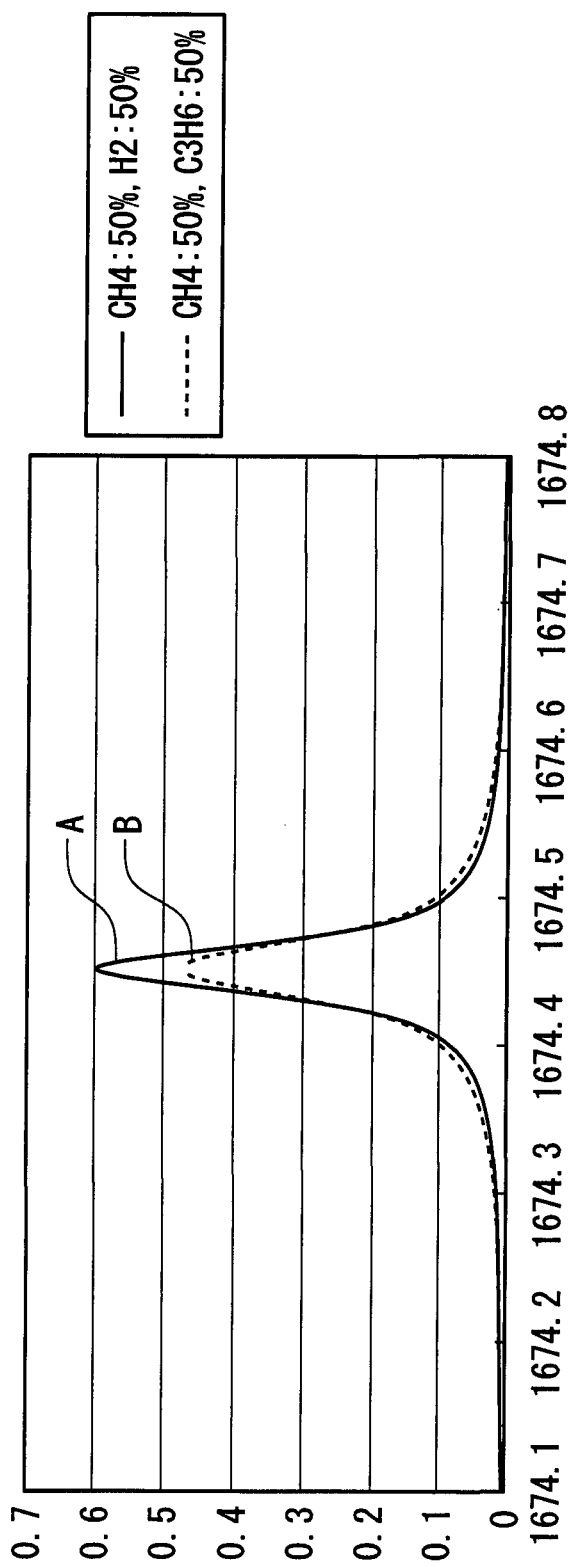
FIG. 14 is a view of an example in which the peak width changes due to the difference of component gases.

A specific example in which the peak width changes will be described using FIG. 14. FIG. 14 is a view of an example in which the peak width changes due to the difference of component gases, only the absorption spectrum of methane is extracted by removing absorptions of other than methane. In FIG. 14, Characteristic A indicates the spectrum of a mixed gas of 50% of methane and 50% of hydrogen, and Characteristic B indicates the spectrum of a mixed gas of 50% of methane and 50% of propylene. As is evident from FIG. 14, the peak width becomes wider when methane is mixed with propylene compared to when methane is mixed with hydrogen.

Figure 15:
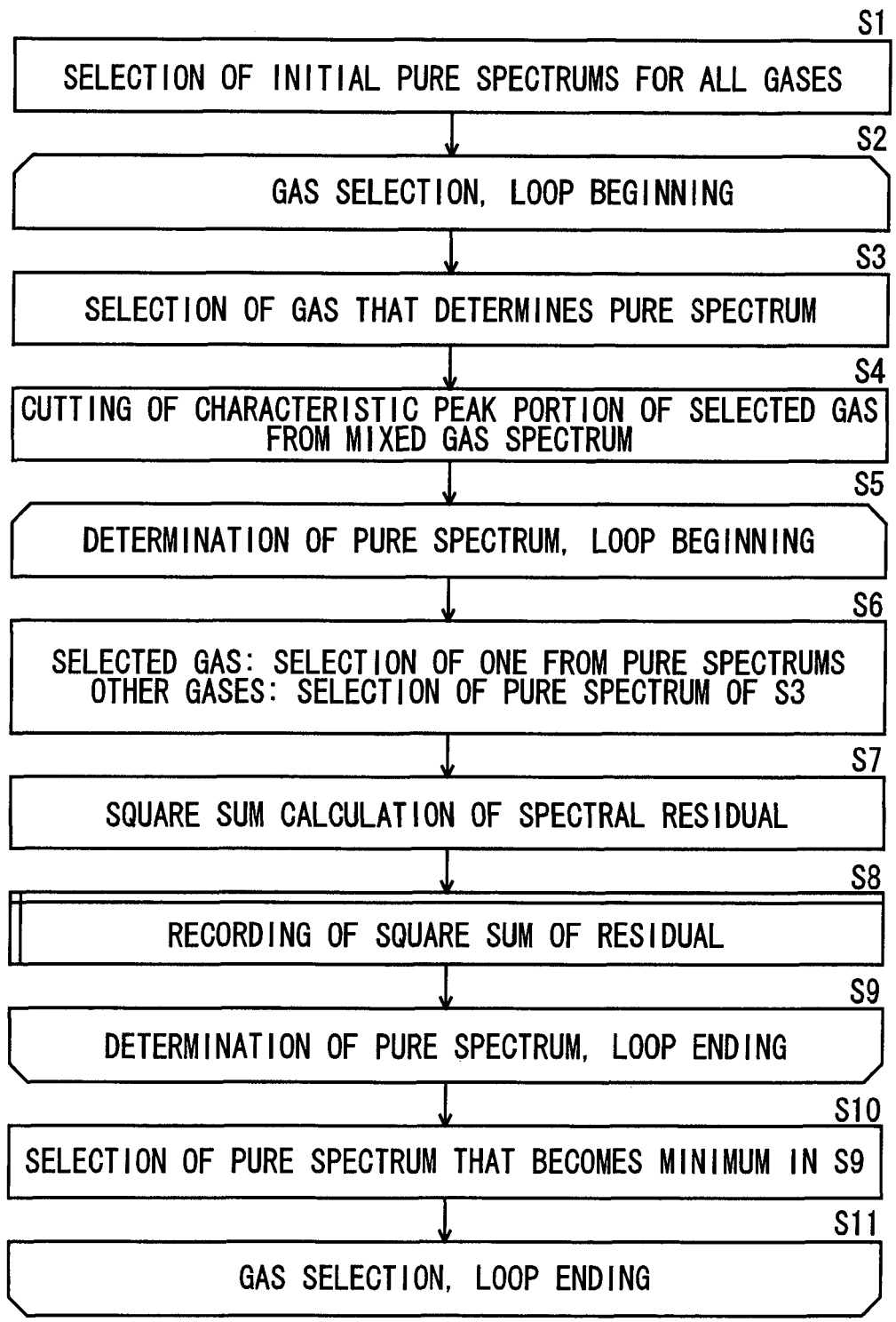
FIG. 15 is a flowchart of a sequence for selecting a proper spectrum from the database.

In order to deal with the change in the spectrum shape, the absorption spectrums of the respective gases to be measured which are most similar to the actual spectrum shape are selected from a spectrum database obtained in advance using a processing sequence method shown in the flowchart of FIG. 15. In order to select an absorption spectrum which is similar to the spectrum shape, the spectrum database should include the absorption spectrums of a variety of shapes.

The cause for a change in the spectrum shape is considered to be frequent occurrence of molecular collision. That is, propylene or propane having a large collision cross-sectional area of molecules has a large effect of changing the spectrum shape. On the other hand, examples of molecules having a small effect of changing the spectrum shape include a nitrogen molecule having a small collision cross-sectional area of molecules.

Based on the above reason, a spectrum database is built by measuring a number of spectrums for which the mixing ratio of a combination of two kinds of components in the mixed gas shown below is changed, and a spectrum having the most similar spectrum shape is selected and used from the database.

$CH_4:CH_4+N_2, CH_4+C_3H_6, CH_4+C_3H_8$
$C_2H_4:C_2H_6+N_2, C_2H_4+C_3H_6, C_2H_4+C_3H_8$
$C_2H_6:C_2H_6+N_2, C_2H_6+C_3H_6$
$C_2H_6:C_2H_6+N_2$
$C_3H_8:C_3H_8+N_2$

Based on the flowchart of FIG. 15, a sequence for selecting a proper spectrum from the database will be described. Firstly, the absorption spectrum of each of the respective gases to be measured which is to be used in calculation (hereinafter the initial pure spectrum) is read from the database. Herein, it is not necessary to consider the change in the spectrum shape and the like, and an arbitrary pure spectrum may be used (Step S1).

Next, a gas selection loop begins (Step S2), and a kind of gas that determines the optimal pure spectrum is selected (Step S3). In addition, from a mixed gas spectrum, a wavelength area portion in which the selected gas has characteristic peaks and which is selected in advance is cut out (Step S4).

Subsequently, a pure spectrum determination loop begins (Step S5). With regard to the selected gas, pure spectrums are selected from the database one by one, and, with regard to the spectrum of other than the selected gas, the pure spectrum of Step S1 is selected (Step S6).

Using the pure spectrum, a spectral residual is obtained in the following formula manner.

$$A = CK + R \qquad (5)$$

Here, A represents the mixed gas spectrum, K represents the arrayed pure spectrums of the respective gases, C represents the concentrations (gas partial pressures) of the respective gases, and R represents the spectral residual. Here, when the pure spectrums of the respective gases are determined, the concentrations (gas partial pressures) can be obtained from the formula (5) in the following formula (6) manner.

$$C = AK^T(KK^T)^{-1} \qquad (6)$$

The concentrations (gas partial pressures) obtained in the above manner are again substituted into the formula (5) so as to perform the square sum computation of the spectral residual (Step S7).

After the square sum of the spectral residual is recorded (Step S8), an another pure spectrum is selected for the selected gas, and the square sum of the spectral residual is recorded. The above step is performed on all the pure spectrums of the selected gas (Step S9). Among the square sums of the spectral residual obtained in the above manner, the pure spectrum when the square sum is least is used as the optimal pure spectrum (Step S10).

After the optimal pure spectrum is obtained, the same flow is repeated for the next gas, and the optimal pure spectrums are obtained for all the gases (Step S11).

In Step S6 of FIG. 3, the formula (6) is recalculated in the vicinity of the peaks of the respective gases using the obtained optimal pure spectrums, and the approximately calculated concentrations (gas partial pressures) of the respective gases are obtained. Only the peak of a certain hydrocarbon can be extracted by subtracting the optimal pure spectrum of other gases for the concentration (gas partial pressure) obtained using the formula (6) from the spectrum in the vicinity of the peak selected for the hydrocarbon. For example, in a case in which only ethanol is extracted from the spectrum of a mixed gas of 5 kinds of hydrocarbons (methane, ethylene, ethane, propylene, and propane), it is allowed to be that.

$$A(C_2H_6)=A-K(CH_4)C(CH_4)-K(C_2H_4)C(C_2H_4)-K(C_3H_6)C(C_3H_6)-K(C_3H_8)C(C_3H_8) \quad (7)$$

When values obtained using the formula (6) in the vicinity of the respective peaks are used as the concentrations (gas partial pressures) of the respective hydrocarbon gases being used in the formula (7), the extraction accuracy increases. The spectrum of ethane which is extracted in the above manner is shown in FIGS. 16A to 16C. FIG. 16A shows the spectrum of the mixed gas, FIG. 16B shows the spectrum of extracted ethane, and FIG. 16C shows the pure spectrum of ethane. As is evident from FIGS. 16A to 16C, while ethane is included only at 15%, a spectrum of ethane having an almost the same shape as the pure spectrum can be extracted.

Meanwhile, in a case in which the influence of a change in the base line remains, the change in the base line can be removed by performing least squares fitting using zero-order (simple offset), first-order (slant offset), and the pure spectrum of ethane. In the invention, correction is made up to the first element so that the absorption spectrums of the respective gases to be measured from which the change in the base line is removed are separated.

In order to calculate the concentrations (gas partial pressures) using the extracted spectrums, the areas of the spectrums are used. When the partial pressures of the respective gases are constant, a region in which the proportional relationship between area and concentration (gas partial pressure) is formed at all times is present even when external environments such as the total pressure and component gases change. The partial pressures of the respective gases are calculated using the area of the region.

Figure 17A:
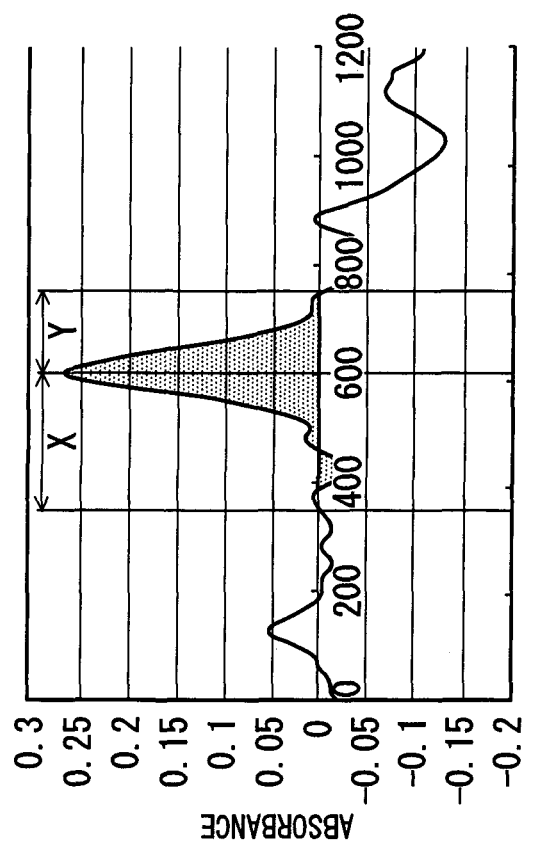
FIGS. 17A and 17B are diagrams for explaining a case in which the spectrum area region of ethylene is determined
Figure 17B:
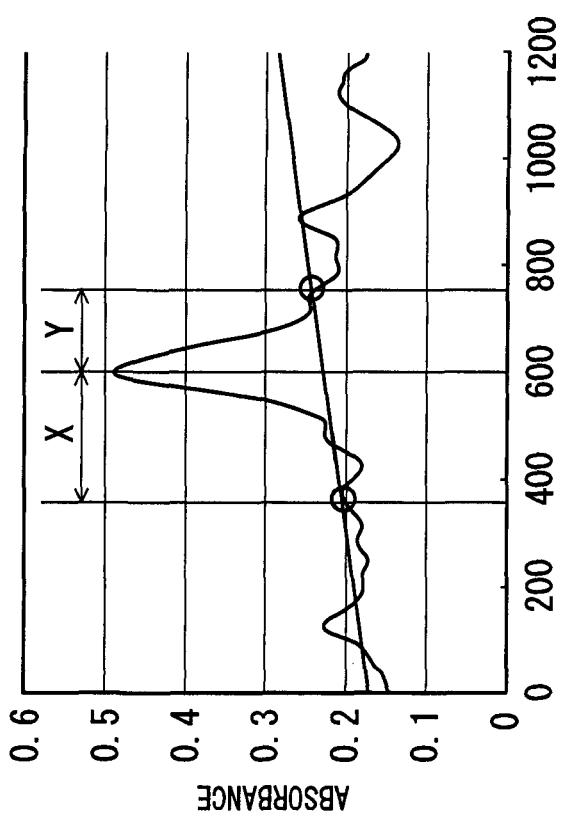

As a specific example, a case in which the spectrum area region of ethylene is determined will be described using FIGS. 17A and 17B. Firstly, in order to subtract the base line portion, for $C_2H_4$, a straight portion connecting two points of the X point on the short wavelength side and the Y point on the long wavelength side of the peak portion is subtracted as shown in FIG. 17A. Thereby, the influence of the change in the base line can be completely removed as shown in FIG. 17B. In addition, the area between the two points is obtained.

Figure 18:
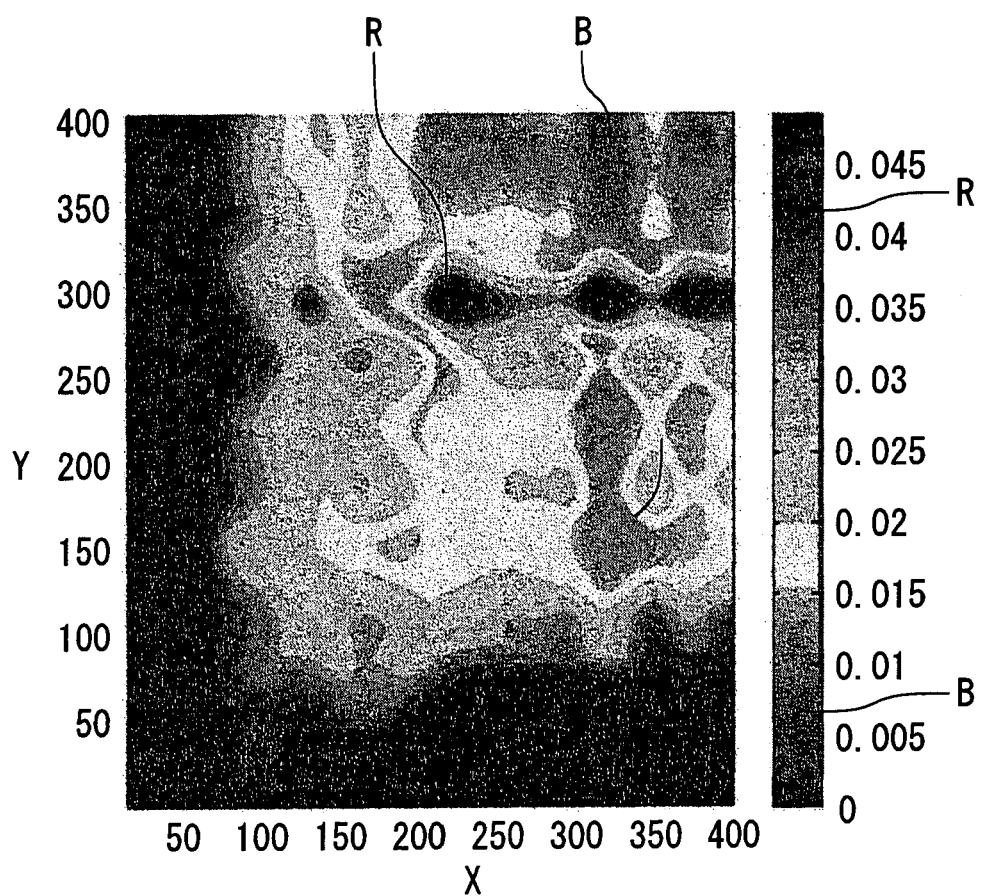
FIG. 18 is an area calculation region view.
Figure 19:
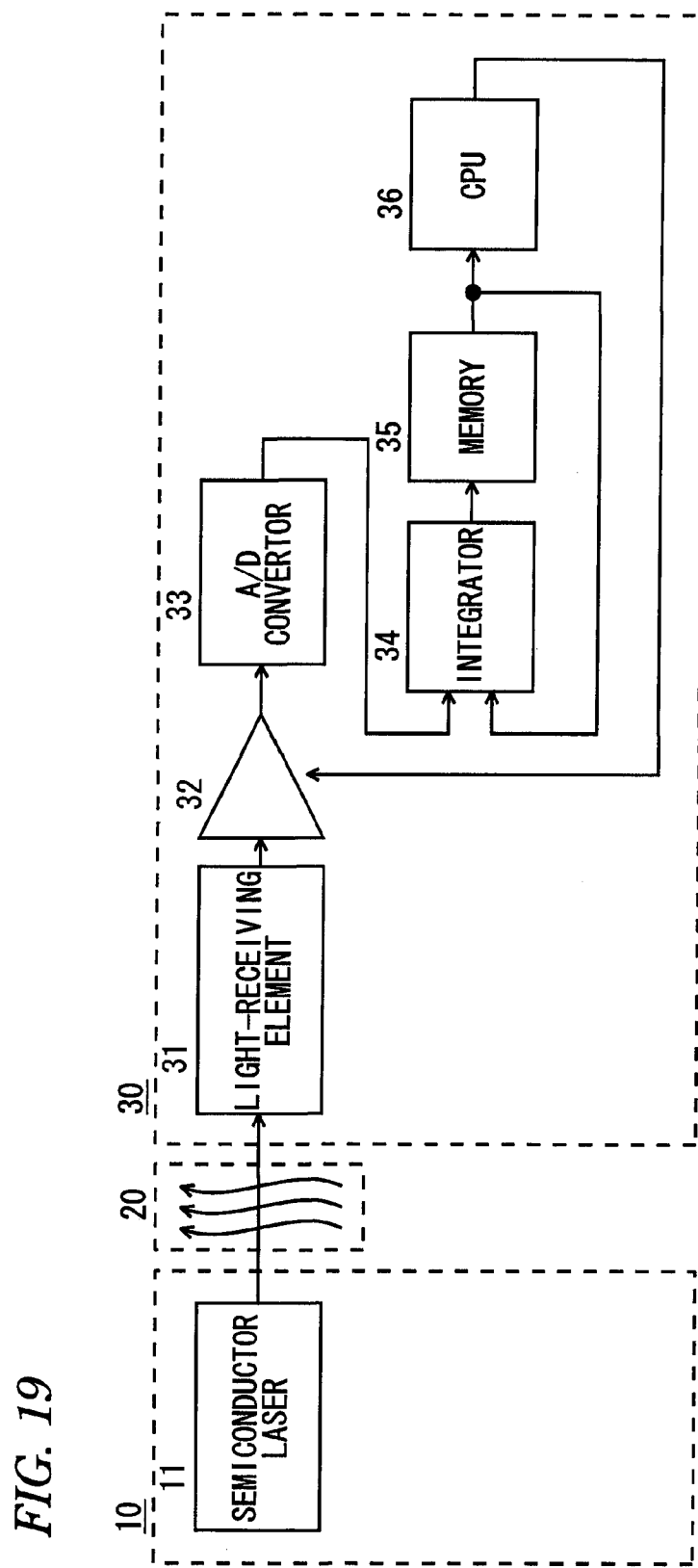
FIG. 19 is a block diagram showing a laser gas analyzer of the related art.

The above processing is performed in the same manner on all the spectrums in the spectrum database for which the concentrations (gas partial pressure) are already known. FIG. 18 is an area calculation region view which shows the result of a combination of X and Y obtained when the relationship between concentration (gas partial pressure) and area is most similar to a proportional relationship by changing the X and Y values in a range of 1 to 400. The horizontal axis corresponds to X, the vertical axis corresponds to Y, the blue portion (B) indicates that the detection error decreases, and the red portion (R) indicates that the detection error increases. For ethylene, a combination of X=317 and Y=373 becomes effective.

A gas chromatography has been mainly used for analyses of hydrocarbon multicomponent systems due to the high component separation capability; however, since the measurement time was long, direct use of measured values for control was not possible. A laser gas analyzer which can measure on a real time basis has a narrow wavelength-variable width of a light source, and is thus limited mainly to measurement of a single component.

In contrast to the above, in the invention, an industrial laser gas analyzer which can measure the absorption spectrum of a multicomponent mixed gas on a real time basis was realized by using a MEMS-VCSEL having no mechanical moving portion, high reliability which is required as an industrial instrument, and a capability of wavelength variation in a wide wavelength range as a light source.

Specifically, a laser gas analyzer which can measure the absorption spectrum of a multicomponent mixed gas on a real time basis and can analyze a hydrocarbon multicomponent mixed gas was realized by using when a MEMS-VCSEL oscillating in a wavelength range of 1620 nm to 1750 nm as a light source.

A precise absorption spectrum can be obtained in a wide wavelength range by performing wavelength calibration using the absorption lines of $CH_4$ and $C_2H_4$.

A case in which it becomes impossible to measure absorption lines that are used for wavelength calibration due to a decrease in the concentrations (gas partial pressures) of gases being used for wavelength calibration among the gases to be measured can be avoided by using the wavelength calibrating gas cell 117 in which $CH_4$ and $C_2H_4$ are sealed.

In an analyzer of the related art, the wavelength calibrating gas cell 117 is inserted into a path for the reference light separated at the beam splitter 105; however, in the invention, the wavelength calibrating gas cell 117 is placed ahead of the beam splitter 105 so that wavelength calibration and light output calibration can be performed at one light-receiving element. In addition, the absorption signals of a calibrating gas can be subtracted from the absorption signals of the gases to be measured by simply performing division of the absorption signals of the gases to be measured obtained from the photodiode 108 and the reference signals obtained from the photodiode 110.

An accurate absorption spectrum is obtained by performing the wavelength calibration of the absorption spectrum of the hydrocarbon multicomponent mixed gas obtained using the absorption lines of $CH_4$ and $C_2H_4$ of the wavelength calibrating gas and the wavelength table.

The absorption spectrum of each of the respective gases is obtained by separating the absorption spectrums of the respective components using the absorption spectrum database of the respective components in the hydrocarbon multicomponent mixed gas.

It become unnecessary to obtain a calibration curve for each application and excessive engineering man-hours can be decreased by developing and employing the area method in which the statistical method (chemometrics) is not used as a module for obtaining the concentrations (gas partial pressures) of the respective components from the absorption spectrum of a multicomponent system. Thereby, the absorption spectrum of each of the respective gases can be obtained, and the concentrations (gas partial pressures) of the respective gases can be obtained without using the statistical method (chemometrics).

In order to use the area method, it is necessary to separate the absorption spectrum of each of the respective gases to be measured from the overlapped absorption spectrum of the mixed gas; however, in the invention, least squares fitting was performed in a wavelength band in which the characteristic absorption lines of the respective gases are present using the absorption spectrum database including even the change in the absorption spectrum shape due to mixing of gases, and the absorption spectrum of each of the respective gases to be measured were separated from the absorption spectrum of the mixed gas. Thereby, the influence of the absorption of other gases can be suppressed to an extent of the change in the base line.

In the invention, since a method in which an area is obtained by subtracting a value determined from the shape of absorption lines from the absorption spectrum is employed as the area method, the influence of the change in the base line can be removed.

It became unnecessary to prepare calibration curves by using wavelength regions in which absorption of other hydrocarbon gases was small and absorption of impurities was small as the peaks of the respective hydrocarbon gases.

A change in the spectrum shape could be dealt with by selecting the most appropriate spectrum for the actual spectrum shape from the spectrum database, whereby robustness improved.

It became possible to highly accurately measure the concentrations (gas partial pressures) by using the area of a region in which the concentration (gas partial pressure) error decreases even when the spectrum shape changed.

Meanwhile, depending on the concentration (gas partial pressure) value, there is a possibility that other gas spectrums increase in the vicinity of the selected peaks such that the extraction error increases. In such a case, peaks being used may be changed depending on the concentration (gas partial pressure) values of the mixed gas.

The temperature of the gases to be measured inputted to the gas cell 106 is desirably set to be constant using the gas temperature controller 119. Thereby, a change in the spectrum shape accompanying a change in the temperature can be suppressed, and the measurement error due to a change in the temperature can be reduced.

When the optical system is configured using an optical fiber, restrictive conditions in designing can be mitigated so as to achieve miniaturization, and stability with respect to mechanical vibrations can be increased.

Application to gases that are not easily absorbed or detection of a small amount of gas becomes possible by providing multiple paths so as to extend the light path length.

The gases to be measured may be depressurized and measured. Thereby, separation of overlapped absorption lines can be expected.

Time-division measurement is also possible at a common light-receiving element by using plural wavelength-variable light sources.

The wavelength calibrating gas is not limited to $CH_4$ and $C_2H_4$, and $C_2H_4$ or HCl may also be used depending on the wavelength band which is used for measurement. Examples of the wavelength calibrating gas being used include gases of molecules having a small number of atoms and sharp absorption lines, gases which are the same gases to be measured, isotopes of the gases to be measured, or gases having a similar composition which has absorption lines in a close wavelength range. For example, when the spectrum of the hydrocarbon is measured, wavelength calibration is performed using a hydrocarbon having one or two carbon atoms.

The total pressure of the wavelength calibrating gas is desirably depressurized in order to sharpen the absorption lines being used for calibration. Particularly, more highly accurate measurement becomes possible through depressurization so that the overlapping of plural absorption lines is solved and separated. For example, when methane is used for wavelength calibration, it is effective to decrease the total pressure to 0.1 atmospheres or less since the overlapping of plural absorption lines is solved.

The absorption rate of the wavelength calibrating gas cell 117 is desirably set to $1/10$ or less of the absorption rate of the gas cell 106 in order to decrease the influence on the S/N of measurement signals.

As described above, according to the invention, a laser gas analyzer in which a wavelength-variable laser having a wide wavelength-variable width as a laser light source is used, and the concentrations of the respective components included in the hydrocarbon multicomponent mixed gas can be measured relatively easily using the area method that does not depend on the statistical method can be realized, which is effective for direct measurement of a variety of process gases.

What is claimed is:
1. A laser gas analyzer comprising:
a wavelength-variable laser having a wavelength-variable width;
a calibrating gas cell in which wavelength calibrating gas is sealed, wherein the light of the wavelength-variable laser is made to be incident to the calibrating gas cell;
a light-split module configured to split an output light of the calibrating gas cell into a measurement light and a reference light, the reference light is for wavelength calibration;
a first gas cell into which gases to be measured are introduced, wherein the measurement light is made to be incident to the first gas cell;
a photoelectric section configured to convert the reference light and an output light of the first gas cell into electrical signals; and
a data processor configured to obtain an absorption spectrum of each of the gases to be measured based on a reference signal related to the reference light and an absorption signal related to the output light of the first gas cell, and to obtain concentrations of the respective gases to be measured based on areas of the absorption lines of the gasses to be measured, wherein the data processor includes;
an absorption line wavelength data storage configured to store absorption line wavelength data of the gases to be measured;
a wavelength calibrator into which the reference signal and the absorption signal are inputted and which is connected to the absorption line wavelength data storage, configured to calibrate wavelength of the absorption spectrum based on the absorption line wavelength data, the reference signal, and the absorption signal, and to obtain an absorption spectrum of an absorbance by performing division of the wavelength-calibrated reference signal and the absorption signal;

an absorption spectrum data storage configured to store absorption spectrum data of the gases to be measured;

a spectrum separator into which the absorption spectrum of the absorbance is inputted from the wavelength calibrator and which is connected to the absorption spectrum data storage, and configured to separate the absorption spectrum of the absorbance of each of the gases to be measured from the absorption spectrum of the absorbance;

an area-to-concentration ratio data storage configured to store wavelength range data used for calculating areas of the absorption lines of the gases to be measured and to store proportional constant data of the area and gas partial pressure; and a concentration detector into which the absorption spectrum of each of the gases to be measured is inputted from the spectrum separator and which is connected to the area-to-concentration ratio data storage, configured to obtain an area of a designated wavelength range, and to calculate partial pressures of the gases to be measured.

2. The laser gas analyzer according to claim 1, wherein the wavelength calibrator is configured to compare an absorption line of a wavelength calibrating gas and known absorption line.

3. The laser gas analyzer according to claim 2, wherein the wavelength calibrator is configured to compare the absorption line of the wavelength calibrating gas and the known absorption line using polynomial approximation.

* * * * *